(12) United States Patent
Kim

(10) Patent No.: US 11,344,227 B2
(45) Date of Patent: *May 31, 2022

(54) APPAREL WITH ULTRASONIC POSITION SENSING AND HAPTIC FEEDBACK FOR ACTIVITIES

(71) Applicant: NIKE, Inc., Beaverton, OR (US)

(72) Inventor: Ernest Kim, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/918,302

(22) Filed: Jul. 1, 2020

(65) Prior Publication Data
US 2020/0334962 A1     Oct. 22, 2020

Related U.S. Application Data

(63) Continuation of application No. 16/039,711, filed on Jul. 19, 2018, now Pat. No. 10,720,032, which is a
(Continued)

(51) Int. Cl.
*H04B 3/36* (2006.01)
*A61B 5/11* (2006.01)
(Continued)

(52) U.S. Cl.
CPC ............ *A61B 5/1114* (2013.01); *A41D 1/002* (2013.01); *A61B 5/0816* (2013.01); *A61B 5/486* (2013.01);
(Continued)

(58) Field of Classification Search
CPC ..... A61B 5/1114; A61B 5/0816; A61B 5/486; A61B 5/6804; A61B 5/002; A61B 5/1135;
(Continued)

(56) References Cited

U.S. PATENT DOCUMENTS 6,308,565 B1   10/2001   French et al.
6,571,193 B1   5/2003   Unuma et al.
(Continued)

FOREIGN PATENT DOCUMENTS

KR   1020050072558   7/2005
WO   2017095951   6/2017

OTHER PUBLICATIONS

"International Application Serial No. PCT US2016 064257, International Search Report dated Mar. 13, 2017", 3 pgs.
(Continued)

*Primary Examiner* — Zhen Y Wu
(74) *Attorney, Agent, or Firm* — Schwegman Lundberg & Woessner, P.A.

(57) ABSTRACT

An article of apparel, a system, and methods include a fabric configured to conform to a body of a wearer. A plurality of ultrasonic positioning sensors are secured with respect to the fabric at a first set of predetermined locations, each of the ultrasonic positioning sensors configured to emit a sound wave configured to be detected by other ones of the plurality of ultrasonic positioning sensors and output an electronic signal indicative of having emitted or detected a sound wave. A plurality of feedback devices secured with respect to the fabric at a second set of predetermined locations, each of the feedback devices configured to output a feedback signal configured to be detectable by the wearer of the article of apparel.

21 Claims, 9 Drawing Sheets

Related U.S. Application Data continuation of application No. 15/365,815, filed on Nov. 30, 2016, now Pat. No. 10,055,948.

(60) Provisional application No. 62/260,988, filed on Nov. 30, 2015.

(51) Int. Cl.

| | | |
|---|---|---|
| *A41D 1/00* | (2018.01) | |
| *A61B 5/08* | (2006.01) | |
| *A61B 5/00* | (2006.01) | |
| *G08B 6/00* | (2006.01) | |
| *A41D 13/00* | (2006.01) | |
| *A61B 5/113* | (2006.01) | |
| *A41D 31/18* | (2019.01) | |

(52) U.S. Cl.
CPC .............. *A61B 5/6804* (2013.01); *G08B 6/00* (2013.01); *A41D 13/0015* (2013.01); *A41D 31/18* (2019.02); *A61B 5/002* (2013.01); *A61B 5/1135* (2013.01); *A61B 5/7455* (2013.01); *A61B 2503/10* (2013.01); *A61B 2562/0204* (2013.01); *A61B 2562/046* (2013.01)

(58) Field of Classification Search
CPC .............. A61B 5/7455; A61B 2503/10; A61B 2562/0204; A61B 2562/046; A41D 1/002; A41D 31/18; A41D 13/0015; G08B 6/00
USPC ...................................................... 340/407.1
See application file for complete search history.

(56) References Cited

U.S. PATENT DOCUMENTS

| | | | | |
|---|---|---|---|---|
| 7,012,521 | B2* | 3/2006 | Fardin ....................... | G01S 5/30 |
| | | | | 340/539.13 |
| 7,602,301 | B1* | 10/2009 | Stirling .............. | A63B 69/3623 |
| | | | | 340/573.1 |
| 7,625,316 | B1 | 12/2009 | Amsbury et al. | |
| 8,253,586 | B1* | 8/2012 | Matak ..................... | G06F 17/00 |
| | | | | 340/870.07 |
| 8,798,763 | B2* | 8/2014 | Forsell .................... | H02J 50/80 |
| | | | | 607/61 |
| 9,582,072 | B2* | 2/2017 | Connor ................. | A61B 5/6831 |
| 9,855,005 | B2* | 1/2018 | Cheng .................. | A61B 5/0064 |
| 10,055,948 | B2 | 8/2018 | Kim | |
| 10,720,032 | B2 | 7/2020 | Kim et al. | |
| 2003/0154792 | A1* | 8/2003 | Katayama ................ | G01C 9/00 |
| | | | | 73/602 |
| 2003/0216228 | A1 | 11/2003 | Rast | |
| 2005/0222638 | A1* | 10/2005 | Foley .................. | A61N 1/36007 |
| | | | | 607/40 |
| 2009/0051544 | A1 | 2/2009 | Niknejad | |
| 2009/0256801 | A1* | 10/2009 | Helmer ................... | G06F 3/011 |
| | | | | 345/156 |
| 2010/0201500 | A1* | 8/2010 | Stirling ................ | A61B 5/1124 |
| | | | | 340/407.1 |
| 2012/0136254 | A1* | 5/2012 | Kim ....................... | G06F 1/1601 |
| | | | | 600/443 |
| 2014/0005547 | A1* | 1/2014 | Balasubramanian .. | A61B 8/467 |
| | | | | 600/447 |
| 2014/0031703 | A1* | 1/2014 | Rayner .............. | A61B 5/02055 |
| | | | | 600/484 |
| 2014/0039316 | A1* | 2/2014 | Ichioka .................. | A61B 8/483 |
| | | | | 600/439 |
| 2014/0111414 | A1* | 4/2014 | Hayner ................... | G06F 1/163 |
| | | | | 345/156 |
| 2014/0135644 | A1* | 5/2014 | Kim ..................... | A61B 5/6803 |
| | | | | 600/545 |
| 2014/0228649 | A1* | 8/2014 | Rayner ................... | G16H 20/30 |
| | | | | 600/301 |
| 2014/0276242 | A1* | 9/2014 | Chen ..................... | A61B 5/1116 |
| | | | | 600/595 |
| 2015/0145656 | A1* | 5/2015 | Levesque ................ | G06F 3/016 |
| | | | | 340/407.1 |
| 2015/0145671 | A1* | 5/2015 | Cohen ................ | G08B 13/2445 |
| | | | | 340/539.11 |
| 2015/0239573 | A1* | 8/2015 | Jouper ................... | B64D 11/06 |
| | | | | 701/3 |
| 2015/0309563 | A1* | 10/2015 | Connor ................ | A61B 5/1071 |
| | | | | 73/865.4 |
| 2015/0366504 | A1* | 12/2015 | Connor ................ | A61B 5/6804 |
| | | | | 600/301 |
| 2015/0370320 | A1* | 12/2015 | Connor ................ | A61B 5/1126 |
| | | | | 345/173 |
| 2016/0089078 | A1* | 3/2016 | Du ........................ | A61B 5/024 |
| | | | | 600/301 |
| 2016/0262687 | A1* | 9/2016 | Vaidyanathan ...... | A61B 5/1121 |
| 2016/0278444 | A1* | 9/2016 | Jordan ................... | A41D 1/002 |
| 2016/0310064 | A1* | 10/2016 | Cheng ...................... | A61B 5/11 |
| 2017/0071468 | A1* | 3/2017 | La Pietra ............... | G16H 40/63 |
| 2017/0154505 | A1 | 6/2017 | Kim | |
| 2017/0196513 | A1* | 7/2017 | Longinotti-Buitoni ..................... | |
| | | | | A61B 5/6805 |
| 2017/0229041 | A1* | 8/2017 | Reichow ................ | G09B 9/052 |
| 2017/0231490 | A1* | 8/2017 | Toth ..................... | A61B 5/1075 |
| | | | | 600/558 |
| 2017/0311874 | A1* | 11/2017 | Simonetti ............ | A61B 5/6829 |
| 2018/0108225 | A1 | 4/2018 | Mappus et al. | |
| 2018/0322746 | A1 | 11/2018 | Kim | |
| 2020/0391078 | A1 | 12/2020 | Cusey et al. | |

OTHER PUBLICATIONS

"International Application Serial No. PCT US2016 064257, Written Opinion dated Mar. 13, 2017", 9 pgs.
"U.S. Appl. No. 15/365,815, Non Final Office Action dated Nov. 14, 2017", 16 pgs.
"U.S. Appl. No. 15/365,815, Examiner Interview Summary dated Feb. 6, 2018", 3 pgs.
"U.S. Appl. No. 15/365,815, Response filed Feb. 14, 2018 to Non Final Office Action dated Nov. 14, 2017", 9 pgs.
"U.S. Appl. No. 15/365,815, Notice of Allowance dated Apr. 13, 2018", 10 pgs.
"International Application Serial No. PCT US2016 064257, International Preliminary Report on Patentability dated Jun. 14, 2018", 11 pgs.
"U.S. Appl. No. 15/365,815, Corrected Notice of Allowability dated Jul. 24, 2018", 2 pgs.
"U.S. Appl. No. 16/039,711, Non Final Office Action dated Feb. 15, 2019", 20 pgs.
"U.S. Appl. No. 16/039,711, Examiner Interview Summary dated Mar. 19, 2019", 3 pgs.
"U.S. Appl. No. 16/039,711, Response filed May 15, 2019 to Non Final Office Action dated Feb. 15, 2019", 11 pgs.
"U.S. Appl. No. 16/039,711, Final Office Action dated Jun. 3, 2019", 17 pgs.
"U.S. Appl. No. 16/039,711, Response filed Aug. 5, 19 to Final Office Action dated Jun. 3, 2019", 11 pgs.
"U.S. Appl. No. 16/039,711, Advisory Action dated Aug. 21, 2019", 2 pgs.
"U.S. Appl. No. 16/039,711, Non Final Office Action dated Oct. 24, 2019", 18 pgs.
"U.S. Appl. No. 16/039,711, Examiner Interview Summary dated Nov. 19, 2019", 3 pgs.
"U.S. Appl. No. 16/039,711, Notice of Allowance dated Mar. 11, 2020", 10 pgs.
"U.S. Appl. No. 17/003,249, Preliminary Amendment filed Aug. 27, 2020", 8 pgs.
Hullinger, Jessica, "These Vibrating Yoga Pants Will Correct Your Downward Dog", Fast Company and Inc, (Jan. 15, 2016), 6 pgs.
"U.S. Appl. No. 17/003,249, Non Final Office Action dated Jan. 26, 2022", 12 pgs.

* cited by examiner

| TIME | $D_{A-B}$ | $D_{A-C}$ | $D_{A-D}$ | $D_{A-E}$ | $D_{A-F}$ | ... | $D_{A-C}:$ $D_{A-E}$ | ... | TOL. | FEED-BACK |
|---|---|---|---|---|---|---|---|---|---|---|
| 1 | 40 | 70 | 105 | 110 | 135 | ... | 0.636 | ... | ... | ... |
| 2 | 42 | 70 | 108 | 110 | 140 | ... | 0.636 | ... | ... | ... |
| 3 | 44 | 72 | 110 | 112 | 145 | ... | 0.643 | ... | ... | ... | though alternative sensors
APPAREL WITH ULTRASONIC POSITION SENSING AND HAPTIC FEEDBACK FOR ACTIVITIES

CLAIM OF PRIORITY

This application is a continuation application of Ser. No. 15/365,815, filed Nov. 30, 2016, which application claims the benefit of priority of U.S. Patent Application Ser. No. 62/260,988, filed on Nov. 30, 2015, which is incorporated by reference herein in its entirety.

TECHNICAL FIELD

The subject matter disclosed herein generally relates to an article of apparel with a ultrasonic position detection and haptic feedback based on activities.

BACKGROUND

Articles of apparel, such as shirts, jackets, pants, footwear, and the like, have long been customized for use with particular activities. While certain activities support any of a range of types of articles of apparel, from loose-fitting to conformal, other activities are conventionally performed or conducted in relatively conformal for form-fitting apparel. For instance, aerobic exercises, acrobatics, yoga, and many other activities are commonly performed in tight-fitting apparel and various articles of apparel have been designed to provide such a conformal fitting.

BRIEF DESCRIPTION OF THE DRAWINGS

Some embodiments are illustrated by way of example and not limitation in the figures of the accompanying drawings.

DETAILED DESCRIPTION

Example methods and systems are directed to an article of apparel with a ultrasonic position detection and haptic feedback based on activities. Examples merely typify possible variations. Unless explicitly stated otherwise, components and functions are optional and may be combined or subdivided, and operations may vary in sequence or be combined or subdivided. In the following description, for purposes of explanation, numerous specific details are set forth to provide a thorough understanding of example embodiments. It will be evident to one skilled in the art, however, that the present subject matter may be practiced without these specific details.

Articles of apparel for particular activities have been developed that utilize electronics for various purposes. For instance, yoga apparel has been developed that incorporates haptic feedback devices at specific locations. An external sensor, such as a motion-capture camera, monitors the wearer of the apparel as the wearer engages in predetermined motions and positions. When the wearer deviates from the predetermined motions, the wearer receives a haptic interaction to guide the wearer back into proper position.

However, by relying on external sensors, such systems may have limitations on the capacity to determine what the user is doing and whether or not feedback is called for. For instance, while a camera may provide views of a front aspect of a user, the camera may not have views of the side and rear of the user. Even the use of multiple cameras may still result in portions of the body that may not be viewable all the time, particularly as the wearer twists and otherwise performs the prescribed actions.

An article of apparel has been developed that provides for haptic feedback to guide a wearer through an activity that has integrated sensors. In various examples, the integrated sensors are ultrasonic sensors, though alternative sensors that operate on related, distance and direction-finding principles, may be utilized as well. The ultrasonic sensors are placed at predetermined locations on the article of apparel, conforming to locations of particular relevance to the activity. Based on the output of the sensors and data concerning how the sensors should be in relation to one another, a controller outputs signals to haptic devices to signal the wearer to adjust a position, motion, or other aspect of their activity.

Figure 1A:
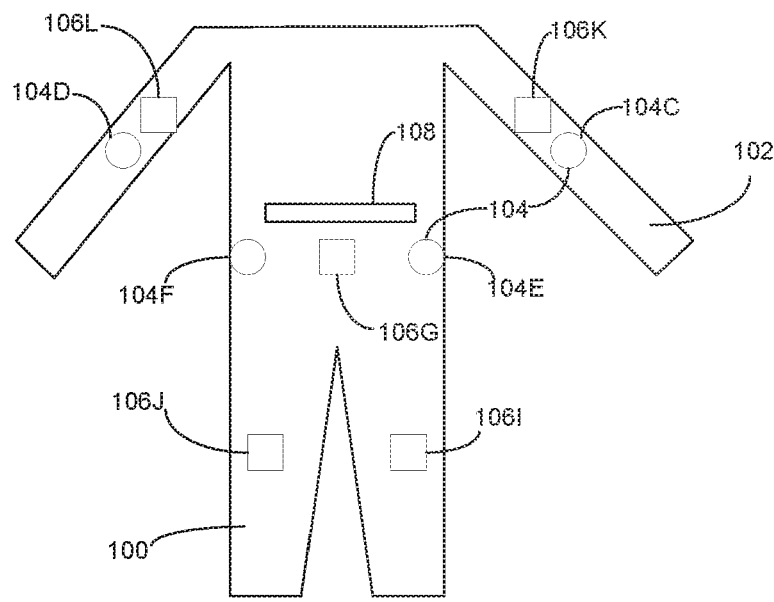
FIGS. 1A and 1B are front and back depictions, respectively, of an article of apparel including various electronic devices, in an example embodiment.
Figure 1B:
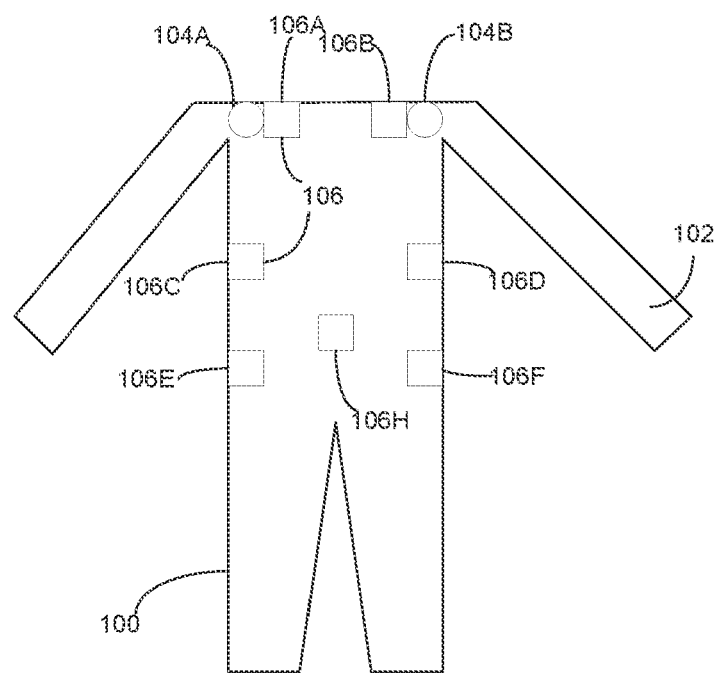

FIGS. 1A and 1B are front and back depictions, respectively, of an article of apparel 100 including various electronic devices, in an example embodiment. The article of apparel 100 includes a fabric 102 base made from an elastane or other stretchable synthetic fiber or any fiber, textile, or material that may provide for the article of apparel 100 to be conformal to the wearer's torso and, in the illustrated full-body example, the wearer's body generally. The article of apparel 100 further includes multiple positioning sensors 104 configured to generate electronic outputs indicative of a relative position of the positioning sensors 104 with respect to one another, as will be disclosed in detail herein. In various examples, the positioning sensors 104 are or include ultrasonic sensors. In the illustrated example, the positioning sensors 104 are positioned at six discrete locations: left shoulder sensor 104A; right shoulder sensor 104B; left arm sensor 104C; right arm sensor 104D; left side sensor 104E; right side sensor 104F. It is noted that, while the various positioning sensors 104 are depicted as affirmatively being on either the front or the back of the article of apparel 100, various examples allow for the positioning sensors 104 to be on the front, back, or sides of the article of apparel 100. Furthermore, the number and configuration of positioning sensors 104 on the article of apparel 100 may be selectively adapted to the desired activities and the degree of positioning precision desired, including by locating positioning sensors on the legs of the article of apparel 100, such as at the knees.

The article of apparel 100 further includes feedback devices 106 configured to provide a sensory output discernable to a wearer of the article of apparel 100. In various examples, the feedback devices 106 are haptic feedback devices. In various examples, the haptic feedback devices are comprised of one or more individual haptic motors or other haptic devices, such as electroactive polymers, each positioned to be separately discernable to the wearer. In various examples, each feedback device 106 includes from one (1) to five (5) individual haptic motors, though it is emphasized that in other examples as many haptic motors may be included in each feedback device 106 as desired. Furthermore, the individual feedback devices 106 may alternatively or additionally include alternative feedback elements configured to deliver sensory output to the wearer using alternative mechanisms, including electrical stimulation, heat, sound, light, or any other mechanism as desired. The individual haptic motors and/or other feedback elements may be selectively and individually engaged alone or in combinations to generate different haptic sensations for the wearer.

As illustrated, the feedback devices 106 are positioned at discrete location on the article of apparel 100 intended to provide feedback to particular locations on the body of the wearer. In various examples, at least some of the locations correspond to predetermined pressure points on the wearer's body that may be identified as being relevant to a given activity. In the illustrated example, the feedback devices 106 include: left shoulder device 106A; right shoulder device 106B; left ribcage device 106C; right ribcage device 106D; left hip device 106E; right hip device 106F; midriff device 106G; tailbone device 106H; left knee device 106; right knee device 106J; left arm device 106K, and right arm device 106L. The corresponding locations may be related to yoga and/or actions or activities typically associated with yoga, among other activities. Individual feedback devices 106 may be omitted or added, as desired.

While the positioning sensors 104 and the feedback devices 106 are not, in this example, depicted as being substantially or completely co-located, in various examples some or all of the positioning sensors 104 and feedback devices 106 are co-located. The positioning sensors 104 and feedback devices 106 may be substantially co-located by being positioned within a short distance of one another, e.g., approximately two (2) to five (5) centimeters, or may be co-located by substantially overlapping one another on the fabric 102. Furthermore, while specific locations for positioning sensors 104 are illustrated, it is to be understood that additional positioning sensors 104 may be utilized as desired. In an example, a positioning sensor 104 is co-located with each feedback device 106.

The article of apparel 100 further optionally includes a respiration sensor 108 positioned so as to detect expansion and contraction of the fabric 102 proximate the ribcage and/or midriff of the wearer of the article of apparel 100. In an example, the respiration sensor 108 is a strain gauge extending laterally across the article of apparel 100. The strain gauge detects increased strain during inhalation and decreased strain during exhalation. The strain gauge specifically, or the respiration sensor 108 generally, may be sensitive to a binary instance in which the wearer breathes as well as the duration of a breath (measured from a particular moment of the detection of an increase in strain or other indication of the start of a breath to a last moment of the detection of the decrease in strain or other indication of the end of a breath), the size or depth of a breath (e.g., based on the magnitude of change between the strain gauge in the relaxed state and a maximum amount of strain measured), the location of a breath (e.g., the largest amount of strain being sensed at the ribcage or at the midriff or belly), and so forth.

Figure 2:
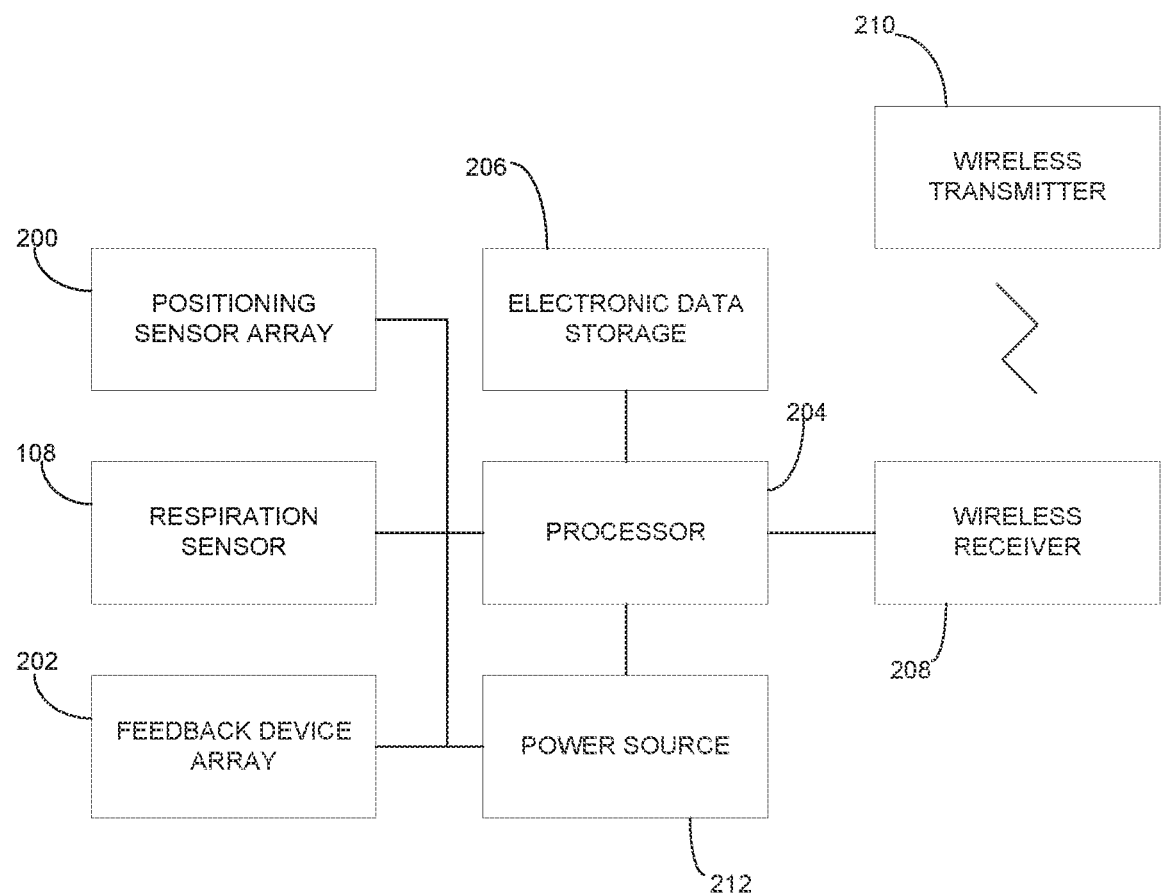
FIG. 2 is a block diagram of electronics of the article of apparel, in an example embodiment.

FIG. 2 is a block diagram of electronics of the article of apparel 100, in an example embodiment. The positioning sensors 104 form a positioning sensor array 200 which, with the data generated form the individual positioning sensors 104, may be utilized to determine an approximate orientation the positioning sensors 104 with respect to one another and, by extension, the posture of the wearer of the article of apparel 100. As will be disclosed in detail herein, the positioning sensor array 200 may produce data over time, allowing both instantaneous position to be determined at a particular time as well as the nature of movement of the positioning sensors 104 over time. Thus, the positioning sensor array 200 may provide data related to a given position as well as the movement that resulted in the position.

The feedback devices 106 are similarly organized in a feedback device array 202. The positioning sensor array 200 and the feedback device array 202 are coupled to a processor 204 configured to receive inputs from each of the positioning sensors 104 and the respiration sensor 108 and transmit commands to feedback devices 106. The processor 204 is configured to utilize the inputs from the positioning sensors 104 and the strain gauge 108 to coordinate the output of the feedback devices 106 based on either a predetermined activity program or concurrently generated input from a remote source, such as a remote trainer.

In an example, the processor 204 is coupled to an electronic data storage 206, such as random-access memory (RAM), read-only memory (ROM), flash memory, and the like. The electronic data storage 206 is optionally configured to store data related to an activity program. In particular, the data related to the activity program specifies positional relationships between and among the positioning sensors 104 and, optionally, respiration parameters that should be sensed by the respiration sensor 108 at particular times during an activity session, as will be disclosed in detail herein. In various examples, the inclusion of the activity program in the electronic data storage 206 may allow the article of apparel 100 to implement feedback via the feedback devices 106 as a standalone unit. However, in various examples, the article of apparel 100 is at least partially or wholly dependent on an external source for the activity parameters and does not necessarily include the storage of the activity program, in whole or in part, in a native electronic data storage 206.

The processor 204 is optionally coupled to a wireless receiver 208, which is configured to communicate with an external wireless transmitter 210. The wireless receiver 208 is configured to receive the activity program described above and herein from the external wireless transmitter 210. The wireless receiver 208 may receive the activity program serially and in real time, specifying what the positioning sensors 104 and/or the respiration sensor 108 should be sensing at that particular time. Additionally or alternatively, the wireless receiver 208 may receive the activity program in whole or in part prospectively, following which the activity program may be stored in whole or in part in the electronic data storage 206 and accessed by the processor 204 as described above. While the wireless receiver 208 is described specifically as a receiver, it is to be understood that the electronics that implement the wireless receiver 208 may be a wireless transceiver and may be configured to transmit wireless signals as well as receive wireless signals.

A power source 212 is coupled to the positioning sensor array 200, the feedback device array 202, the respiration sensor 108, the processor 204, the electronic data storage 206, and the wireless receiver 208 and configured to provide power to those components, as needed. The power source 212 may be or may include a battery or rechargeable battery as well as other power supply components as needed and as known in the art. Additionally or alternatively, the power source 212 may be or may include kinetic energy generators or other sources of power that may draw power from the movement of the article of apparel 100 or environmental conditions.

The processor 204, electronic data storage 206, wireless receiver 208, and the power source 212 are described above as components of the article of apparel 100. In such examples, the process 204, electronic data storage 206, and wireless receiver 208 are secured to or within the fabric 102 and protected against environmental conditions, such as water, sweat, heat, and the like according to conventional mechanisms. Alternatively, some or all of the processor 204, electronic data storage 206, wireless receiver 208, and the power source 212 are components of a mobile device, such as a smartphone, mobile phone, media player, personal digital assistant (PDA), or dedicated external device that is in communicative contact with the positioning sensor array 200, the feedback device array 202, and the respiration sensor 108, as will be disclosed in detail herein.

Figures 3, 4:
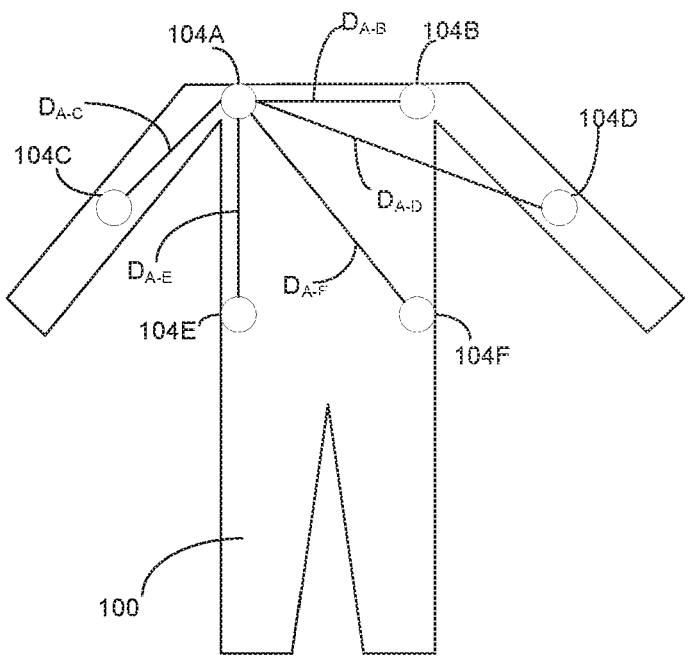
FIG. 3 is an abstract illustration of the function of positioning sensors, in an example embodiment.
FIG. 4 is an abstract rendering of an activity program, in an example embodiment.

FIG. 3 is an abstract illustration of the function of the positioning sensors 104, in an example embodiment. For the purposes of this description, the positioning sensors 104 will be described such that the positioning sensors 104 are or include ultrasonic positioning sensors 104 or other audio-based distance and/or direction sensors. However, it is to be understood that the principles disclosed herein may be applied to any suitable sensors that may be implemented in the article of apparel 100.

Some or all of the positioning sensors 104 are configured to output a sound wave that is detectable by some or all of the other positioning sensors 104. Thus, when the positioning sensor 104A emits a sound wave 300, some or all of the positioning sensors 104B, 104C, 104D, 104E, 104F may sense the sound wave 300. In an example, the positioning sensor 104A transmits an electronic signal to the processor 204 indicating that the sound wave 300 has been emitted, giving the processor 204 a reference time $t_1$ corresponding to the transmittal of the sound wave 300. When one of the other positioning sensors 104B, 104C, 104D, 104E, 104F, in this example positioning sensor 104B, detects the sound wave 300, that positing sensor 104B transmits a signal to the processor 204 indicating that that positing sensor 104B has detected the sound wave, giving the processor 204 a reference time $t_2$ for when the sound wave 300 was detected. The processor 204 may then calculate a distance $D_{A-B}$ between the positioning sensors 104A and 104B by multiplying the time by the speed of sound. As each other positioning sensor 104C, 104D, 104E, 104F detects the sound wave 300 the positioning sensor 104C, 104D, 104E, 104F outputs a signal indicating that the sound wave 300 was detected, allowing the processor to calculate the distance $D_{A-X}$ for each individual positioning sensor 104C, 104D, 104E, 104F that detected the sound wave 300. In cases where a positioning sensor 104B, 104C, 104D, 104E, 104F does not detect the sound wave 300, no distance may be determined for that sensor 104C, 104D, 104E, 104F based on the sound wave 300.

The various positioning sensors 104 may emit sound waves 300 periodically, such as every quarter-second to every two (2) seconds, or on command from the processor 204 based on a determined need for distance data between two or more positioning sensors 104. In various examples, individual positioning sensors 104 do not emit a sound wave 300 at the same time as other positioning sensors 104, though various examples of the positioning sensors 104 may allow for concurrent emission of sound waves 300, for instance where the sound waves 300 are of varying frequency between and among the positioning sensors 104. In various examples, the processor 204 selective induces individual positioning sensors 104 to emit a sound wave 300 based on desired distance data. In further examples, a positioning sensor 104 may emit a "return" sound wave 300 upon sensing the first sound wave 300. Upon the originating positioning sensor 104A detecting the return sound wave 300, the distance between the originating and detecting positioning sensors, e.g., 104A, 104B, respectively, may be determined based on the average of the determined distances $D_{A-B}$ and $D_{B-A}$ or by selecting one of the determined distances, e.g., $D_{A-B}$, as having been corroborated by the other determined distance $D_{B-A}$ being within a predetermined percentage of the first distance $D_{A-B}$.

The positioning sensors 104 may optionally have a directional capability. In particular, a positioning sensor 104 may sense the direction a sound wave 300 was received rather than simply that the sound wave 300 was detected in the first instance. Thus, the output of the positioning sensors 104 may not simply be that a sound wave 300 was detected but the direction from which the sound wave 300 was detected. It will be apparent that the principles related to determined distance between positioning sensors 104 may be adapted to circumstances where direction between individual positioning sensors 104 is also known. In particular, uses of relative distances to determine relative position between positioning sensors 104 may be obviated by the ability of any positioning sensor pair, e.g., 104A and 104C, to know the distance and direction of the other based on detecting a sound wave 300. In such examples, the processor 204 may simply utilize the distance and direction information in comparison with the activity program to provide feedback to the wearer, as disclosed herein, without respect to the distance between and among individual positioning sensors 104.

Provide feedback to a wearer of the article of apparel 100, the processor 204 receives signal from the various positioning sensors 104 and determines the distance D between pairs of positioning sensors 104. These distances D may be visualized in table form, as presented below for the purposes of example and illustration:

TABLE 1

|  | A - Left shoulder | B - Right shoulder | C - Left arm | D - Right arm | E - Left side | F - Right side |
| --- | --- | --- | --- | --- | --- | --- |
| A - Left shoulder | X | 43 cm | 75 cm | 104 cm | 110 cm | 132 cm |
| B - Right shoulder | X | X | 108 cm | 35 cm | 135 cm | 108 cm |

TABLE 1-continued

|  | A - Left shoulder | B - Right shoulder | C - Left arm | D - Right arm | E - Left side | F - Right side |
|---|---|---|---|---|---|---|
| C - Left arm | X | X | X | 102 cm | 51 cm | 68 cm |
| D - Right arm | X | X | X | X | 113 cm | 82 cm |
| E - Left side | X | X | X | X | X | 42 cm |
| F - Right side | X | X | X | X | X | X |

As illustrated in the example of Table 1, sampling the positioning sensors 104 produces distances D between the various positioning sensors 104, while certain pairs of positioning sensors 104, e.g., positioning sensors 104A, 104F, produce no distance data because the positioning sensors 104A, 104F were no within range to detect the sound wave 300 from one another. Table 1 may be updated over time as new distances D are determined between pairs of positioning sensors 104.

While Table 1 includes only one distance between each pair of positioning sensors 104, e.g., $D_{A-B}$ but not $D_{B-A}$, it is emphasized that both distances may be included in various examples of the table. While both distances may be superfluous under various circumstances, conditions where both distances are in fact useful may fully fill out the table.

As noted above, the activity program includes distance parameters that are in effect at various times, as well as respiration and motion parameters as disclosed herein and that may be applied in the same or similar manner as the distance parameters. For a given time in the activity program, the processor 204 cross-references the distances of Table 1 against the distances of the activity program and identifies differences between the distances, as will be disclosed herein. On the basis of the differences, the processor 204 causes the feedback devices 106 to generate a feedback to induce the wearer to adjust their posture or position.

The activity program may be agnostic as to the dimensions of the wearer of the article of apparel 100. That is to say, the activity program may be configured for use by any size wearer or any size article of apparel 100. The activity program and/or the processor 204 may allow for or compensate for differences in dimensions to allow the distances of the activity program to be read on the distances of Table 1.

In an example, the activity program includes baseline distances and the processor 204 conducts a calibration of the distances between the positioning sensors 104 following the wearer donning the article of apparel 100. Thus, in an example, the wearer may be prompted to stand upright with arms relaxed at the sides, whereupon the processor 204 may obtain distances measurements between and among the positioning sensors 104. The processor 204 may compare those distances against calibration distances of the activity program and determine percentage differences between the measured distances and the calibration distances of the activity program. Subsequent distance measurements may be adjusted according to the determined percentages. Thus, if the calibration program determines that the distance $D_{A-C}$ for the wearer is 105% of the calibration distance for that pair while the distance $D_{A-E}$ is 99% of calibration distance for that pair, subsequent measurements of $D_{A-C}$ may be divided by 1.05 and subsequent measurements of $D_{A-E}$ may be divided by 99 before being compared against the distances of the activity program.

Alternatively, the calibration program may be dispensed with in favor of machine learning or other adaptive programs that identify consistent differences between the measured distances and the baseline distances of the activity program. Thus, for instance, the processor 204 may store at least some measured distances in the electronic data storage 206 and periodically retrieve those distances and make comparisons over time. Those comparisons may be compared against distances of the activity program and consistent differences between the measured distances and the distances of the activity program noted. Thus, if over time the difference between the program activity distance and the measured distance for $D_{A-C}$ is 105% as above then the processor 204 may compensate for the measured in $D_{A-C}$ as above.

Further optionally, the distances of the activity program may be based on a size or dimensions of the article of apparel 100. Thus, in an example, where the article of apparel 100 is a size "large" having a predetermined set of dimensions, the distances of the activity program may be greater than where the article of apparel 100 is a side "medium". Similarly, the distances between positioning sensors 104 may be determined empirically for individual articles of apparel 100. Predetermined distances may be adjusted based on calibration mechanisms as described above.

In addition to cross-referencing the actual distances D against the distances of the activity program, the processor 204 may compare other relationships based on the distances D. For instance, a relationship of one distance D to another distance D may be indicative of a two-dimensional relationship of three positioning sensors 104. Thus, for instance, in an example where the wearer is holding their arm above their shoulder, the distance $D_{A-C}$ is measured to be seventy-five (75) centimeters while the distance $D_{A-E}$ is measured to be one hundred ten (110) centimeters. Those distances may be utilized to determine a ratio of those distances of 75/110=0.682. The ratio as determined may be compared against a desired ratio between those two distances from the activity program and utilized to provide feedback, as disclosed herein.

While a relationship between two distances D is described above, it is to be recognized and understood that any relationship between and among the distances D may be utilized. Thus, a relationship between and among three or more distances D may be utilized to establish a relative position of the positioning sensors 104 in three-dimensional space. Moreover, the relationships may be additive, subtractive, or any of a variety of mathematical relationships or concepts as desired.

The relationships may among distances between different times t. Thus, for instance, a relationship may be between the same distance D at different times t. Thus, for instance, the relationship may be the change in $D_{A-C}$ between time t=0 and time t=1 second. In such an example, the relationship may be reflective of the rate at which the wearer is moving their arm.

FIG. 4 is an abstract rendering of an activity program 400, in an example embodiment. The activity program 400 includes a series of parameter sets 402 of specified distances D and/or relationships over time 404. Each parameter set 402 includes one or more distances D and/or relationships and a specified value for each distance D and/or relationship. Thus, for instance, a first parameter set 402 applicable to time t=1 second may specify that $D_{A-C}$=seventy (70) centimeters, $D_{A-E}$=one hundred ten (110) centimeters, and the ratio of $D_{A-C}$ to $D_{A-E}$ is 0.636. While some or all of the parameter sets 402 may overlap the values of Table 1, it is noted and emphasized that some or all of the parameter sets 402 may not include all of the values of Table 1 and some or all may include values that are not included in Table 1. Moreover, the values that are included in the parameter sets 402 may change from set 402 to set 402.

In various examples, the processor 204 is configured to compare the distances D and/or relationships between and among the distances D from a time t against a parameter sets 402 of the activity program 400 corresponding to the time 1. Thus, in the above example, at time t=1 second, the processor 204 may obtain positioning sensor 104 data that provides for $D_{A-C}$ of seventy-five (75) centimeters. The activity program 400 has a parameter set 402 corresponding to time t=1 second having $D_{A-C}$ of seventy (70) centimeters. The processor 204 thus determines that the distance $D_{A-C}$ as measured is five (5) centimeters too long. Additionally or alternatively, the processor 204 determines that the distance $D_{A-C}$ as measured is 75/70=107.1% greater than specified in the parameter set 402. Any other mathematical relationship between the value of the parameter set 402 and the measured value from the positioning sensors 104 may be determined and utilized.

The processor 204 compares each value of the parameter set 402 of the corresponding time t with the measured values from the positioning sensors 104. If a measured value is not available, for instance where one positioning sensor 104 could not detect the sound wave 300 from another positioning sensor 104, then that comparison may be disregarded by the processor 204.

Each parameter set 402 may further specify a tolerance for a value. Thus, for instance, $D_{A-C}$ may have a tolerance of seven (7) centimeters or ten (10) percent. The tolerances may differ from value to value. Thus, $D_{A-E}$ may have a tolerance often (10) centimeters. Additionally or alternatively, the parameter set 402 may specify multiple tolerances over a range that correspond to a degree of difficulty or precision required, e.g., with greater tolerances for lower difficulty and lower tolerances for higher difficulty. A user of the article of apparel 100 may specify, through various suitable mechanisms, a desired difficulty and the corresponding tolerances utilized as appropriate. Alternatively, the parameter set 402 may not specify tolerances with the processor 204 instead applying tolerances as stored in the electronic data storage 206 or obtained from an alternative source.

The parameter set 402 may further specify a feedback program based on the measured values not being within the tolerances of the parameter set 402 values. To the extent that one or more measured or calculated values from the positioning sensors 104 is outside of the corresponding tolerance of the parameter set 402 value, the processor 204 may cross-reference the out-of-tolerance value(s) against the specifications for feedback to the wearer of the article of apparel 100.

For instance, if the wearer of the article of apparel 100 has his or her arm relatively too high for a given parameter set 402 of the activity program 400 then one or more of $D_{A-C}$ and $D_{A-E}$, and a resultant ratio between them, may be out of tolerance. The parameter set 402 further include a specification that, in this example, in the event that the ratio between $D_{A-C}$ and $D_{A-E}$ is out of tolerance that the wearer should receive a feedback to induce the wearer to correct the position of their arm. The parameter set 402 may specify simply that the wearer should "lower arm" or an equivalent command and the processor 204 may interpret that command and cause the feedback devices 106 to deliver a feedback that corresponds to that desired effect. Additionally or alternatively, the parameter set 402 may specify specific feedback devices 106 that should deliver feedback to the wearer and the processor 204 may simply cause the specified feedback devices 106 to deliver the feedback.

It is noted and emphasized that the principles described herein with respect to the positioning sensors 104 and the activity program 400 apply as well to any other sensors that are utilized, including the respiration sensor 108. Thus, the parameter set 402 may further specify a respiration value, such as a rate of expansion or contraction of the ribcage and/or an absolute state of the ribcage (e.g., a circumference of the ribcage), and a tolerance for that respiration value. To the extent that the respiration value as measured is outside of the tolerance, the parameter set 402 may specify either that feedback should be delivered as determined by the processor 204 or may specify the specific feedback that should be given.

The feedback may be customized depending on the all of the determined values together. Thus, if the values indicate that the right arm is too high and the left hip is too far away from the center of mass of the wearer, then either the parameter set 402 may specify or the processor 204 may determine the feedback pattern that would be expected to produce a response where the wearer lowers their arm and moves their hip in. The feedback may simply be a combination of the feedback for each of those desired effects individually or may be different feedback, either by adding a new feedback device 106 to the feedback or by subtracting a feedback device 106 from the feedback, in comparison with simply combining the basic feedback devices 106 of the two desired effects individually. The specific combination of feedback devices 106 that are used to provide the feedback may be determined empirically.

The feedback is, in various examples, based on stimulating pressure points with the feedback devices 106 positioned at those pressure points that tend to produce a desired response. Thus, in the above example where the wearer's left arm is too high, the feedback may be provided by the left shoulder device 106A and the right ribcage device 106D. In such an example, the feedback devices 106A and 106D may deliver a haptic stimulation to the wearer that may trigger a response, variously either voluntary in whole, in part, or involuntary, to lower the left arm. The degree of haptic stimulation from any one feedback device 106 may be the same under all circumstance or may vary, for instance depending on the degree to which a measured value is out of tolerance, with relatively more simulation corresponding to relatively large variations from tolerance and so forth.

As described herein, the processor 204 is configured to obtain data from the positioning sensors 104 and the respiration sensor 108 variously either on an ongoing basis or on demand. In an example, the processor 204 may maintain the application of feedback from the various feedback devices 106 until the measured values are within the tolerances of the currently relevant parameter set 402. Thus, in various examples, the processor 204 may stop the feedback because the wearer has brought the measured values back within the tolerances of the original parameter set 402 or because the parameter set 402, which was active at time t, is no longer active at time 1S and has been replaced by a following parameter set 402 that is active at time 12. In other words, the feedback may stop when the wearer changes their posture or when the activity program 400 moves on to a different action or position.

Figure 5:
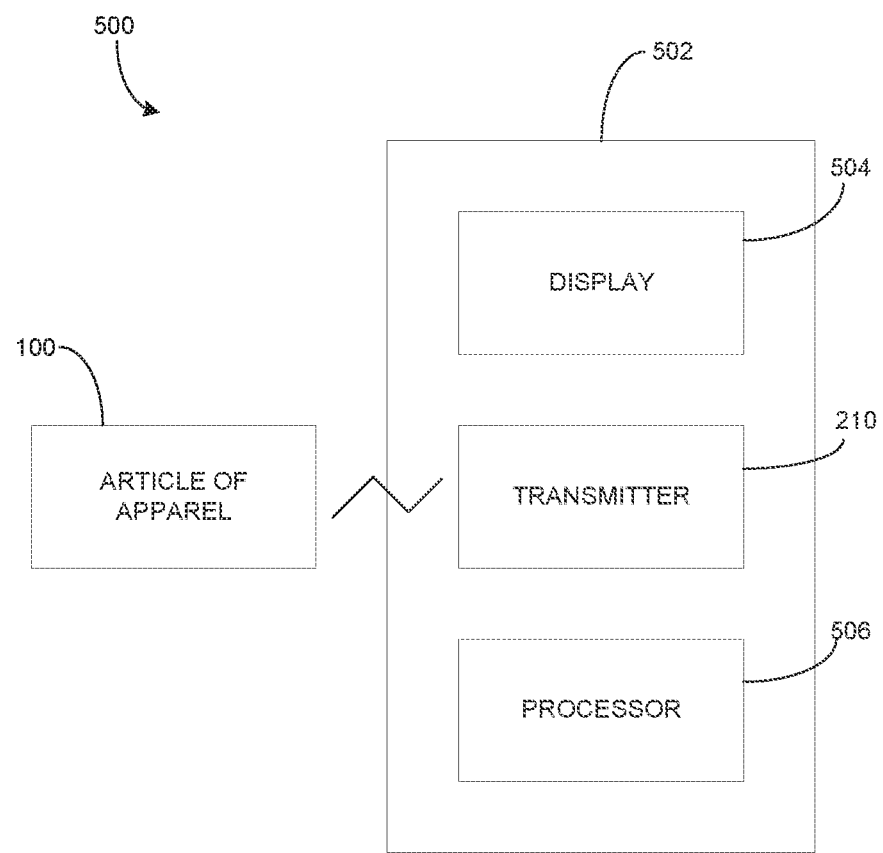
FIG. 5 is a block diagram of a system including the article of apparel, in an example embodiment.

FIG. 5 is a block diagram of a system 500 including the article of apparel 100, in an example embodiment. The system 500 includes an external device 502 configured to display content related to the activity program 400 on a display 504. In various examples, the content is a video of the activity related to the activity program 400. Thus, in an illustrative example related to yoga education, the content is a yoga instructional video. The instructional video, in such an example, includes an image of an instructor or animated representation of an instructor who assumes or otherwise directs the wearer of the article of apparel 100 to assume certain yoga poses or conduct activities or exercises related to yoga, such as breathing exercises. The activity program 400 is synched with the video, such that individual parameter sets 402 that are active at different times correspond to the positions or exercises that are being instructed on by the instructor in the video. Thus, to the extent that the wearer of the article of apparel 100 is not following the instruction on the video, that is detected by the positioning sensors 104 and the respiration sensors 108, identified by the processor 204 based on a comparison with the parameter set 402, and corrective feedback is delivered via the feedback devices 106.

The external device 502 and/or the system 500 generally includes the transmitter 210. The external device 502 further includes or is coupled to a processor 506 that is, in various examples, configured to cause the transmitter 210 to transmit the activity program 400 to the transmitter 208 and to the processor 204. As noted herein, the activity program 400 may be transmitted in a single block, smaller blocks but at least some including multiple parameter sets 402, or may stream individual parameter sets 402 substantially in real time as those parameter sets 402 pertain to the video as the video is being shown on the display 504. In the streaming example, the processor 204 may utilize as the parameter set 402 whatever parameter set 402 the processor 204 has most recently received from the external device 502.

In the above example, the activity program 400 is essentially fixed to a predetermined video instruction program. In such an example, the activity program 400 is predetermined and now subject to change. However, it is to be recognized that the external device 502 may function as a remote interface for an instructor who is giving live instruction at a distance from the article of apparel 100, e.g., not within the same room or general vicinity. In such an example, the activity program 400 may be generated in real time based on the actions of the instructor. In various examples, the instructor may wear another article of apparel 100 and the inputs sensed from the positioning sensors 104 and/or the respiration sensor 108 may be utilized as the parameters for generating a parameter set 402 at any given time. The parameter set 402 as generated may be transmitted to the processor 204 of the wearer and utilized as disclosed herein. Thus, in such examples, the activity program 400 may be generated on an ongoing basis from whatever the instructor is doing at the time.

Figure 6A:
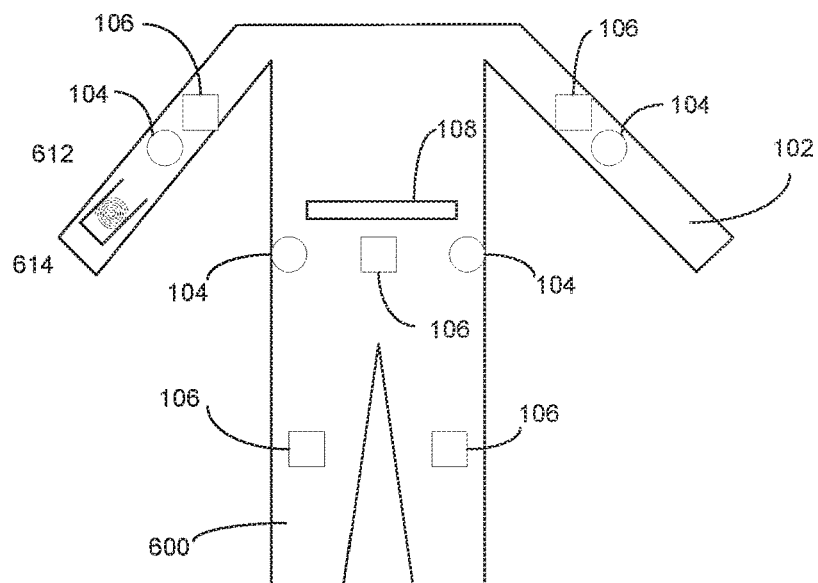
FIGS. 6A and 6B are a depiction and a block diagram of an alternative example of an article of apparel and related system, in an example embodiment.
Figure 6B:
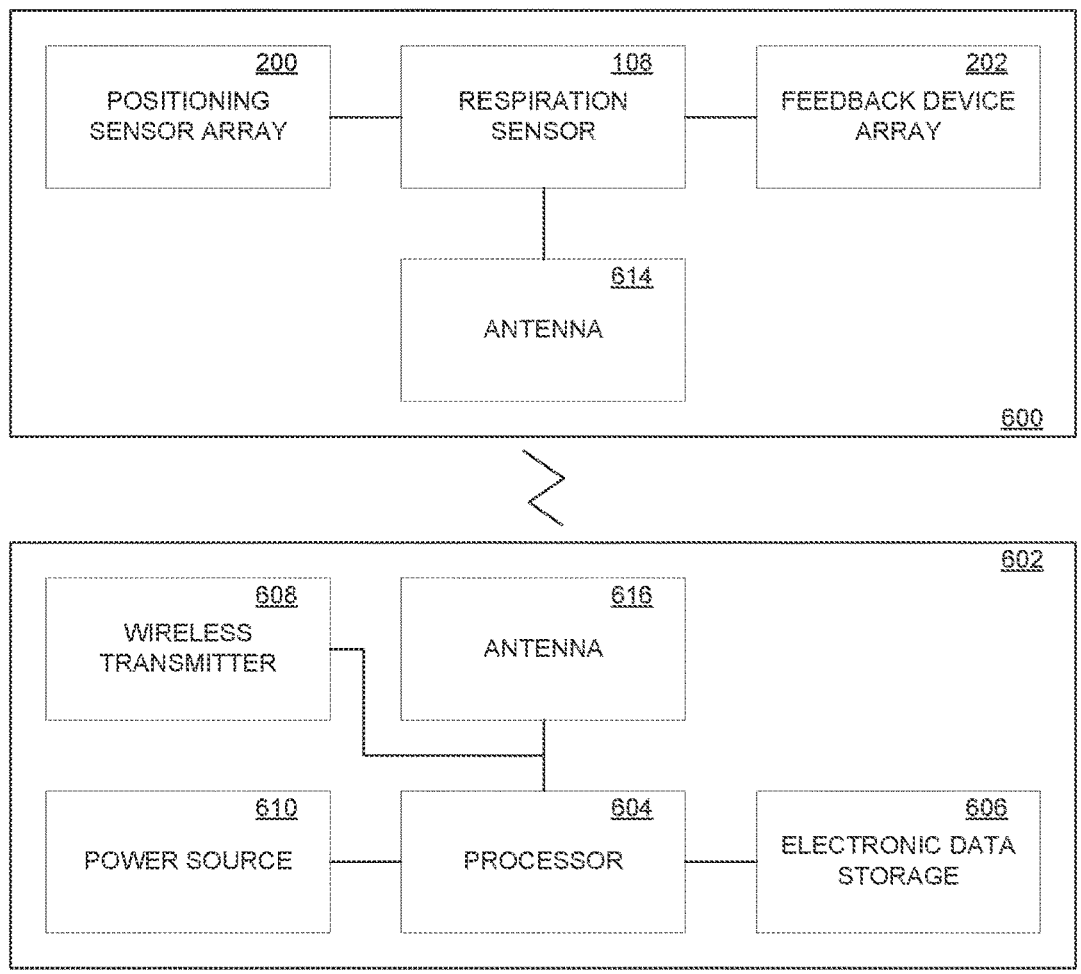

FIGS. 6A and 6B are a depiction and a block diagram of an alternative example of an article of apparel 600 and related system 601, in an example embodiment. The system 601, including the article of apparel 600, may include the same or similar functionality as the article of apparel 100 but utilizes a mobile device 602 having various components instead of having those components native to the article of apparel 600, including a processor 604 in lieu of the processor 204, electronic data storage 606 in lieu of the electronic data storage 206, wireless transmitter 608 in lieu of the wireless transmitter 208, and a power source 610 in lieu of the power source 212. Instead, the article of apparel 600 includes a mobile device fixation element 612 and a short range antenna 614 configured to communicate with a short range antenna 616 of the mobile device 602. In various examples, the fixation element 612 is a pocket or other mechanism configured to substantially secure the mobile device 602 in place with respect to the short range antenna 614 and, in particular, to promote efficient wireless coupling between the short range antennas 614, 616.

In this example, the positioning sensors 104 and respiratory sensor 108 transmit data to the mobile device 602 by way of the antennas 614, 616. The processor 604 performs the processing functions previously attributed herein to the native processor 204. Those functions include, but are not limited to, determining the distances D and other calculated values, comparing those against the activity program 400 and the active parameter set 402, and then transmitting back feedback to be implemented by the feedback devices 106. In general, the mobile device 602 obtains the activity program from the external device 502 and in general conducts provides the active computation, power, and long range computing functions in lieu of native components of the article of apparel 600.

In an example, the antennas 614, 616 are configured for wireless communication according to near field communication (NFC) standards and practices, including in the 13.56 megahertz (MHz) ban according to the ISO/IEC 18000-3 standard promulgated in 2010 or according to any other suitable wireless communication standard that has been or may be developed. The antenna 614 may be coupled to or be a part of an NFC tag. The NFC tag may include an electronic data storage, controller, transceiver, power source, and various other electronics needed or suitable for NFC communications. The tag may be passively powered and derives its operational energy from the wireless signal received from the antenna 614, along with the positioning sensors 104, the feedback devices 106, and the respiration sensor 108. In various examples, the tag may be or may be replaced with any suitable electronics that are configured to receive power from the mobile device 602.

Figure 7A:
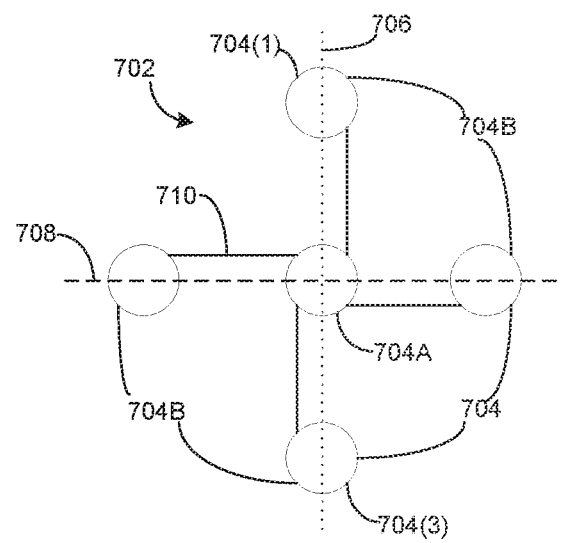
FIGS. 7A-7C are illustrations of examples of arrangements of particular feedback devices.
Figure 7B:
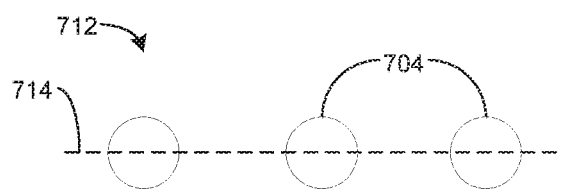
Figure 7C:
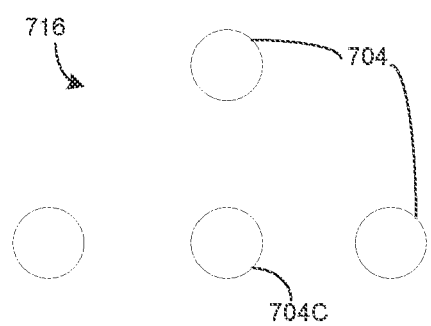

FIGS. 7A-7C are illustrations of examples of arrangements of particular feedback devices 106. In these examples, each of the feedback devices 106 is an array of individual haptic motors positioned to create sensations for a wearer of the article of apparel 100, 600 that are intended to indicate or induce desired actions related to the activity.

FIG. 7A is an example of a shoulder array 702 that may be used for one or both of the left shoulder device 106A and the right shoulder device 106B or as any of the other feedback devices 106 as appropriate. The shoulder array 702 includes five motors 704, including a central motor 704A and four peripheral motors 704B. The motors form a first axis 706 (as illustrated, a vertical axis) and a second axis 708

(as illustrated, a horizontal axis), each with three individual motors 704 forming a generally straight line. The shoulder array 702 is configured to create various haptic feedback sensations in a wearer of the article of apparel 100, 600 by pulsing the motors in combination and/or in sequence. In an example, the motors 704 are separated from one another by a distance D of approximately eight (8) centimeters and/or approximately three (3) inches, though alternative distances D are contemplated in various examples.

In various examples, the motors 704 pulse in sequence along one or the other of the axes 706, 708. Pulsing the motors 704 in sequence includes, in an example, pulsing a first motor 704(1) on an axis 706, followed by the central motor 704A, followed by a third motor 704(3). In various examples, the sequence may involve multiple motors 704 pulsing simultaneously as the sequence progresses along the axis 706, e.g., by the central motor 704A beginning pulsing before the first motor 704(1) ceases pulsing. In various examples, only one motor 704 may pulse at once, with the first motor 704(1) ceasing pulsing before the central motor 704A begins pulsing.

In an example, pulsing the motors in sequence along the vertical axis 706 may tend to convey to the wearer of the article of apparel 100, 600 a sensation of raising or falling/lowering, depending on the sequence, and may tend to induce the wearer to raise or lower their shoulder or back. In an example, pulsing the motors in sequence along the horizontal axis 708 may tend to convey a sensation of twisting the shoulder or arm in a direction according to the sequence. Additionally, the motors 704 may be pulsed in any other sequence without respect to the axes 706, 708 to convey various other types of haptic sensations to the wearer, including spiral or circular patterns and/or patterns that involve delivering haptic signals from multiple motors 704 simultaneously.

As illustrated, the motors 704 of the shoulder array 702 are electrically coupled with respect to one another via wired connections 710. The wired connections 710 may be any suitable direct, electrically conductive connection, including conventional wires as well as electrically conductive thread or any other suitable direct connection mechanism. Further, the motors 704 have a wired connection to a positioning sensor 106 associated with the shoulder array 702. While the positioning sensor 106 is not a component of the shoulder array 702, as noted herein, the positioning sensor 106 is positioned with respect to and associated with the shoulder array 702.

In the illustrated example, the positioning sensor 104 is an ultrasonic device that is further configured to communicate wirelessly with other ultrasonic positioning sensors 106 and/or ultrasonic transmitters/receivers. In various examples, the processor 204 is configured to communicate with the positioning array 200 by emitting or causing a positioning sensor 104 to emit sound waves 300 that include data. The data may cause individual motors 704 within the array 702 to generate haptic stimulation that is perceivable by the wearer. Upon receipt of the ultrasonic signal, the positioning sensor 106 interprets a command included in the data and causes, via the wired connection 710, individual motors 704 to deliver haptic stimulation according to the command, including according to predetermined patterns. Thus, in such an example, the individual haptic devices 106 may be controlled by the processor 204 by wireless signals while, within the arrays (e.g., the shoulder array 702 illustrated here as well as other arrays disclosed herein), individual motors 704 are coupled via wired connections. However, it is noted and emphasized that any or all of the devices 106 and/or the individual motors 704 may be have wired or wireless couplings, as desired.

FIG. 7B is an illustration of a linear array 712 that may be adapted for use in some or all of the devices 106, example embodiments. In an example, some or all of the left ribcage device 106C, the right ribcage device 106D, and the tailbone device 106H may be linear arrays 712 of motors 704. Additionally or alternatively, multiple individual devices 106 may be implemented as a single linear array 712. Thus, in an example, the left ribcage devices 106C and the left hip device 106E may be implemented as a single linear array 712 running down the left side of the article of apparel 712.

Various implementations of the linear array 712 may include varying numbers of individual motors 704, as desired and as utilized on the article of apparel 100, 600. Thus, in an example, where the linear array 712 is configured to function as the combination of the left ribcage device 106C and the left hip device 106E, the linear array 712 may have three (3), four (4), or more motors 704. By contrast, where the linear array 712 is configured as the midriff device 106G or the tailbone device 106H, the linear array 712 may have as few as two (2) motors 704.

In various examples, the linear array 712 may be positioned in any orientation on the article of apparel 100, 600 provided that the motors 704 are generally positioned along a common axis 714. Thus, the linear array 712 may be generally vertical when implemented as the left ribcage device 106C and generally horizontal when implemented as the tailbone device 106H. Implementations in which the linear array 712 is at a diagonal on the article of apparel 100, 600 is also contemplated.

FIG. 7C is an illustration of a T-array 716 that may be adapted for use in some or all of the devices 106, in an example embodiment. In an example, the left knee device 106I and the right knee device 106J are implemented as T-arrays 716. In an example, a central motor 704C is positioned on the article of apparel 100 such that, when the article of apparel 100 is worn by the wearer, the central motor 704C is approximately 2-3 centimeters and/or one (1) inch above a kneecap of the wearer.

Figure 8:
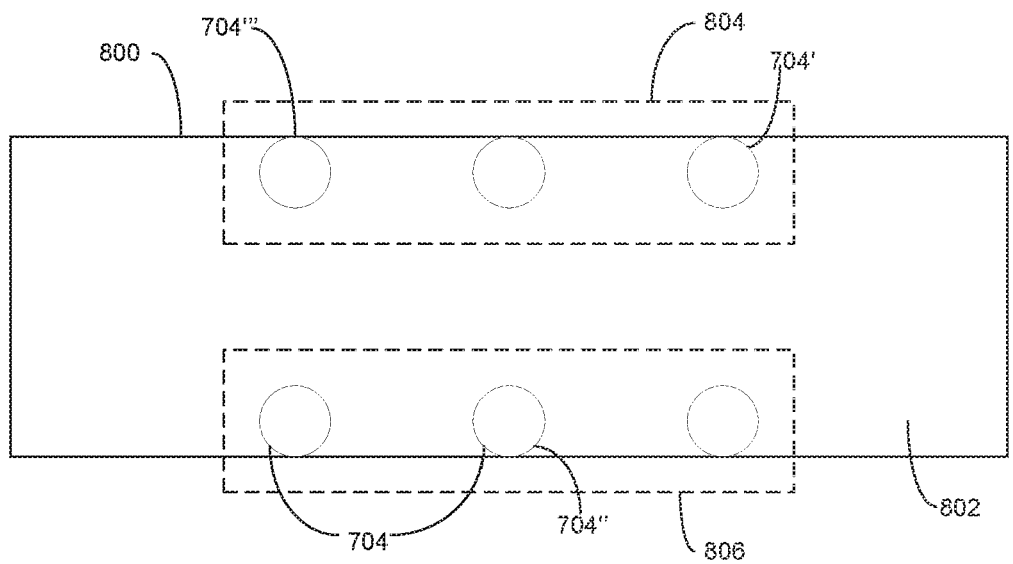
FIG. 8 is an illustration of a sleeve configured to be work over an arm of a wearer and incorporating various devices and functions of the article of apparel, in an example embodiment.

FIG. 8 is an illustration of a sleeve 800 configured to be work over an arm of a wearer and incorporating various devices and functions of the article of apparel 100, 600, in an example embodiment. The sleeve 800 may be worn independently of the article of apparel 100 or may be an integral part of the article of apparel 100. In other words, the sleeve 800 may be the sleeve of the article of apparel 100 or may, as illustrated, be a separate article that may be worn and utilized independently of the article of apparel.

In the illustrated example, the sleeve 800 includes a fabric 802, an anterior array 804 of motors 704 positioned on or within the fabric 802 and a posterior array 806 of motors 704 positioned on or within the fabric 802. As illustrated, the arrays 804, 806 are linear arrays 712 as disclosed herein. In examples where the sleeve 800 is an integral component of the article of apparel 100, sleeve 800 includes an arm positioning sensor 104 as disclosed herein, such as the left arm sensor 104C or the right arm sensor 104D, as appropriate for whether or not the sleeve 800 is a left or right sleeve on the article of apparel 100. Alternatively, the sleeve 800 includes one or more positioning sensors 104 independent of or different than the positioning sensors 104 disclosed herein. In various examples, each of the arrays 804, 806 includes a separate positioning sensor 104 that is also configured to engage in wireless communication with the processor 204 in order to cause individual motors 704 to provide haptic stimulation to the wearer of the sleeve 800.

In various examples, the arrays 804, 806 function as disclosed herein to induce the wearer to perform various movements or actions as disclosed herein. In certain examples, the motors 704 of the different arrays 804, 806 deliver different levels or intensity of haptic stimulation to the wearer. For instance, anterior of the arm may be less sensitive than the posterior of the arm. Thus, in an example, the motors 704 of the anterior array 804 may deliver a more intense haptic stimulation than the motors 704 of the posterior array 806 in order to result in the same perceived intensity by the wearer. This principle applies to the various feedback devices 106 and motors 704 and their corresponding locations generally. Various implementations of the examples disclosed herein may be individually tuned to the particular circumstances and locations in which the motors 704 are utilized.

In various examples, the motors 704 have variable and selectable intensity. In the examples disclosed herein, the sequences and delivery of haptic signals to a wearer may have differing haptic feedback intensity levels that are selectable depending on any of a variety of considerations. For instance, the intensity may be higher the greater the degree to which the wearer deviates from a prescribed motion. Additionally, the intensity may be varied during a sequence or other delivery of haptic stimulation, such as by progressively increasing or decreasing the intensity of the haptic stimulation during an action.

While various examples disclosed herein may tend to operate with the motors 704 of one array not necessarily operating in conjunction with motors 704 of a different array, in various examples, including in the sleeve 800 example, motors 704 between two arrays 804, 806 may operate in conjunction to delivery specified patterns to induce specified actions in a wearer. In an example, a sequence may include a first motor 704' of the anterior array 804 followed by a second motor 706" of the posterior array 806 followed by a third motor 704''' of the anterior array. Such a sequence may be expected to induce a twisting or torqueing motion in an arm of a wearer that might, for instance, be associated with the swinging of a tennis racquet or golf club.

Figure 9A:
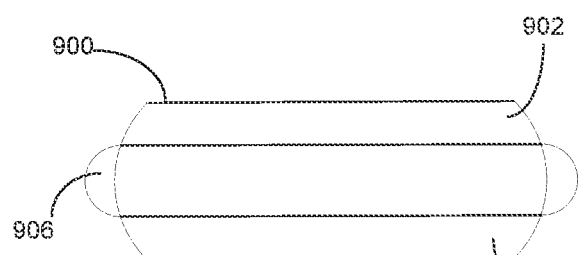
FIGS. 9A and 9B are side and top views, respectively, of a button motor that may function as a haptic motor, in an example embodiment.
Figure 9B:
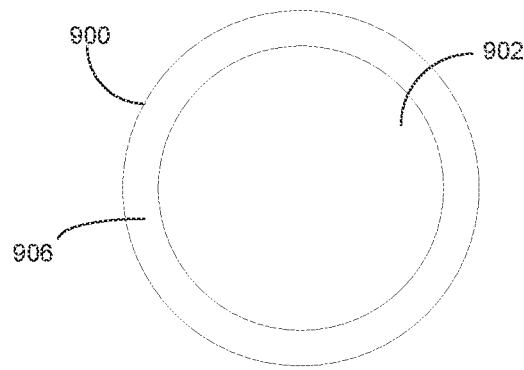

FIGS. 9A and 9B are side and top views, respectively, of a button motor 900 that may function as a haptic motor 704, in an example embodiment. In such an example, the button motor 900 includes a first housing 902 and a second housing 904 enclosing electronics that include a haptic motor itself. One or more electrodes 906 are configured to be electrically coupled to direct connections 710 for the provision of electrical signals to the button motor 900. Additionally, one or both of the housings 902, 904 may conductive and function as electrodes. In various examples, the electrical signals may include commands for the delivery of haptic stimulation and power for operating the electronics. The button motor 900 may be any of a variety of sizes depending on the intensity of the haptic signal to be delivered. In various examples, the button motor 900 is between 1.5 and 3.0 centimeters in diameter and 0.5 to 1.0 centimeters in height.

In various examples, the articles of apparel 100, 600 and/or the sleeve 800 include securing mechanisms for seating and securing button motors 900 in the various locations illustrated herein or anywhere else desired. The securing mechanisms may be pockets, clamps, brackets, or any other mechanism that may create a friction fit with a button motor 900. The securing mechanism may also be configured to bring the electrodes 906 into electrical contact with a direct connection 710 to electrically couple the button motor 900 to an associated array, as disclosed herein.

In an example, the button motor 900 includes a native power source, such as a battery, including but not limited to replaceable or rechargeable batteries, a kinetic energy generator, or other suitable source of power. Additionally or alternatively, the button motor 900 operates on the basis of power supplied by the direct connection 710. In such an example, a single power source for the article of apparel 100, 600, or sleeve 800 may power some or all of the motors 704, or each array individually may include a power source, such as a battery, to which the motors 704 of that array are electrically coupled.

Figure 10:
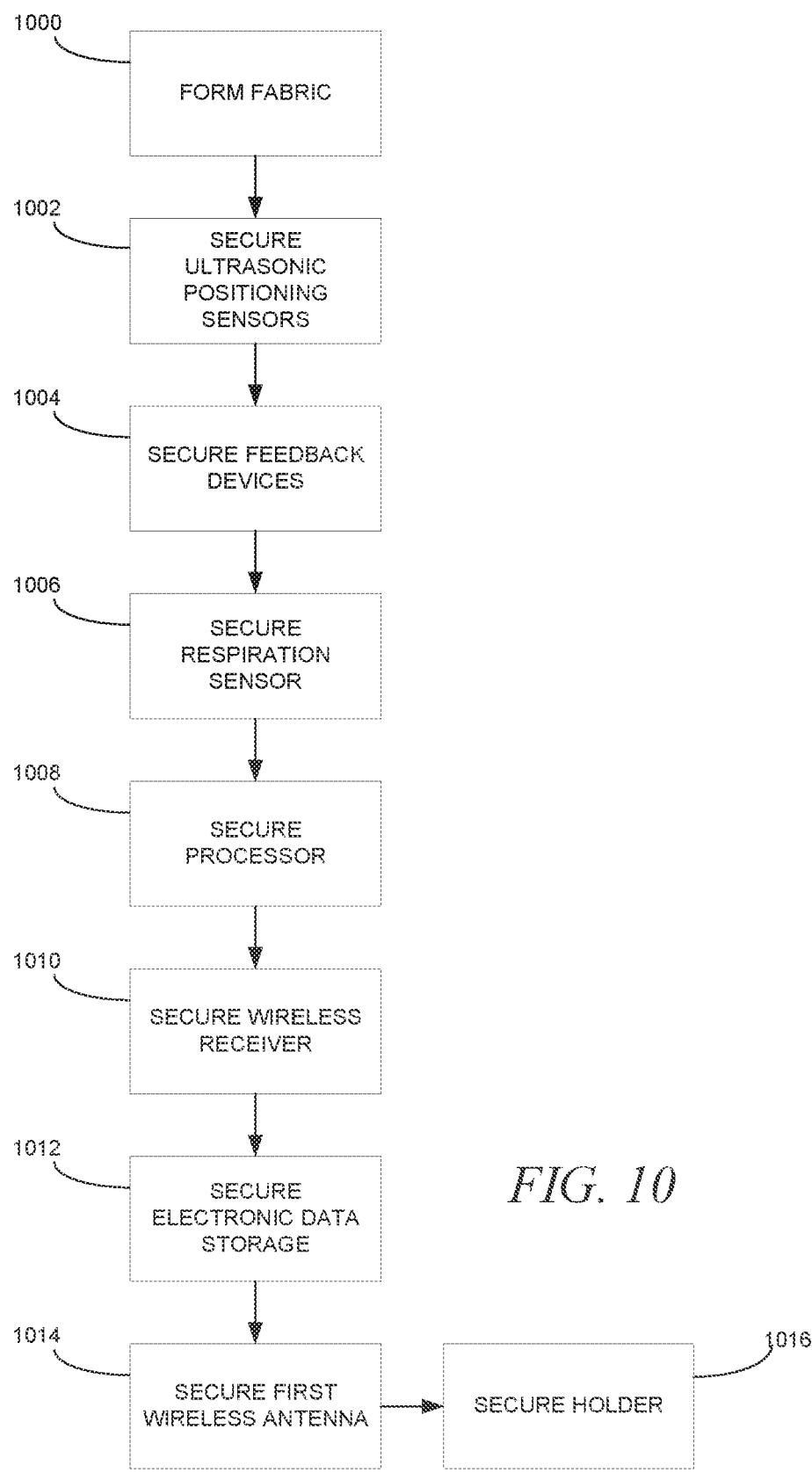
FIG. 10 is a flowchart for making an article of apparel, in an example embodiment.

FIG. 10 is a flowchart for making an article of apparel, in an example embodiment. The article of apparel may be either or both of the articles of apparel 100, 600 or any other suitable article of apparel.

At 1000, a fabric is formed to confirm to a body of a wearer.

At 1002, a plurality of ultrasonic positioning sensors are secured with respect to the fabric at a first set of predetermined locations, each of the ultrasonic positioning sensors configured to emit a sound wave configured to be detected by other ones of the plurality of ultrasonic positioning sensors and output an electronic signal indicative of having emitted or detected a sound wave, the electronic signal configured to be utilized by a processor to determine positional values. In an example, first set of locations comprise a left shoulder, a right shoulder, a left arm, a right arm, a left side, and a right side. In an example, the positional values include a distance between a pair of the plurality of ultrasonic positioning sensors. In an example, the positional values include a ratio of a first distance between a first pair of the plurality of ultrasonic positioning sensors and a second distance between a second pair of the plurality of ultrasonic positioning sensors.

At 1004, a plurality of feedback devices are secured with respect to the fabric at a second set of predetermined locations, each of the feedback devices configured to output a feedback signal configured to be detectable by the wearer of the article of apparel based on a difference between the positional values as determined and a parameter set of an activity program. In an example, each one of the plurality of feedback devices comprises at least one haptic motor. In an example, the second set of locations comprise a left shoulder, a right shoulder, a left ribcage, a right ribcage, a left hip, a right hip, a midriff, a tailbone, a left knee, and a right knee. In an example, individual ones of the plurality of feedback devices are configured to output the feedback signal to induce the wearer of the article of apparel to change posture. In an example, the parameter set comprises at least one target value indicative of a desired distance between two or more of the plurality of positioning sensors, and wherein the individual ones of the plurality of feedback devices are configured to output the feedback signal based on a variation between an associated positional value and the target value. In an example, the target value is associated with a tolerance value and wherein the processor is configured to cause the individual ones of the plurality of feedback devices to output the feedback signal based on the variation exceeding the tolerance value.

In an example, the activity program comprises a plurality of parameter sets, including the parameter set, sequentially organized over time, each discrete period of time corresponding to not more than one of the plurality of parameter sets. In an example, the parameter set comprises at least one target value indicative of a desired distance between two or more of the plurality of positioning sensors, and wherein the processor is configured to cause the individual ones of the plurality of feedback devices to output the feedback signal based on a variation between an associated positional value and the target value. In an example, the activity program is synchronized with an instructional video and wherein individual parameter sets individually correspond to predetermined times in the instructional video. In an example, each individual parameter set is configured to reflect a corresponding instruction at an associated predetermined time in the instructional video.

At 1006, a respiration sensor is secured with respect to the fabric and configured to output a signal based, at least in part, on physiologic factors indicative of respiration of the wearer of the article of apparel. In an example, at least some of the plurality of feedback devices are configured to output the feedback signal based, at least in part, on the signal from the respiration sensor.

At 1008, the processor is optionally secured with respect to the fabric and coupled to the plurality of ultrasonic positioning sensors and the plurality of feedback devices.

At 1010, a wireless receiver is optionally secured with respect to the fabric and coupled to the processor, the wireless receiver configured to receive the activity program from a wireless transmitter.

At 1012, an electronic data storage is optionally secured with respect to the fabric and coupled to the processor, the electronic data storage configured to store the activity program as received by the wireless receiver, wherein the processor is configured to access the activity program from the electronic data storage.

At 1014, a first wireless antenna is optionally secured with respect to the fabric and coupled to the plurality of ultrasonic positioning sensors and the plurality of feedback devices, the wireless antenna configured to establish a wireless connection with a second wireless antenna coupled to the processor, wherein the plurality of ultrasonic positioning sensors and the plurality of feedback devices are communicatively coupleable to the processor via the wireless connection. In an example, the first and second wireless antenna are configured to communicate via a near field communication (NFC) wireless modality.

At 1016, a holder is optionally with respect to the fabric, configured to secure, at least in part, a mobile device, the mobile device comprising the processor and the second wireless antenna.

Figure 11:
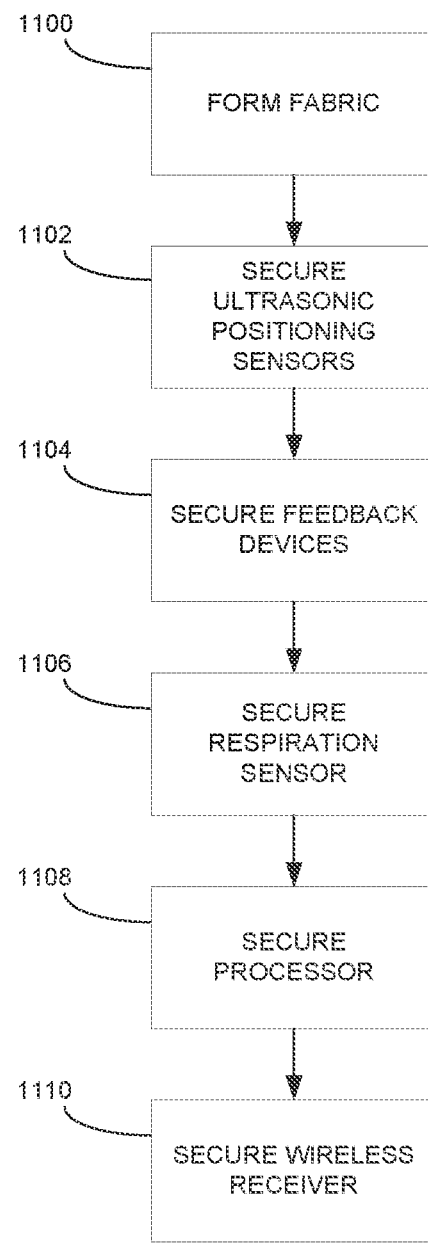
FIG. 11 is a flowchart for using an article of apparel, in an example embodiment.

FIG. 11 is a flowchart for using an article of apparel, in an example embodiment. The article of apparel may be either or both of the articles of apparel 100, 600 or any other suitable article of apparel.

At 1100, an activity program is received from a wireless transmitter. In an example, the activity program comprises a plurality of parameter sets, including the parameter set, sequentially organized over time, each discrete period of time corresponding to not more than one of the plurality of parameter sets. In an example, the parameter set comprises at least one target value indicative of a desired distance between two or more of the plurality of positioning sensors, and wherein causing the individual ones of the plurality of feedback devices to output the feedback signal is based on a variation between an associated positional value and the target value. In an example, the activity program is synchronized with an instructional video and wherein individual parameter sets individually correspond to predetermined times in the instructional video. In an example, each individual parameter set is configured to reflect a corresponding instruction at an associated predetermined time in the instructional video.

At 1102, the activity program is stored in an electronic data storage the activity program as received by the wireless receiver, wherein the processor is configured to access the activity program from the electronic data storage.

At 1104, a wireless connection is established between a first wireless antenna secured to the fabric and a second wireless antenna coupled to the processor, wherein the plurality of ultrasonic positioning sensors and the plurality of feedback devices are communicatively coupleable to the processor via the wireless connection. In an example, establishing the wireless connection is via a near field communication (NFC) wireless modality.

At 1106, a mobile device is secured, at least in part, to the fabric, the mobile device comprising the processor and the second wireless antenna At 1108, positional values of a plurality of ultrasonic positioning sensors secured with respect to a fabric at a first set of predetermined locations are determined with a processor based, at least in part, on electronic signals output by the plurality of ultrasonic positioning sensors, wherein the fabric is configured to conform to a body of a wearer. In an example, the first set of locations comprise a left shoulder, a right shoulder, a left arm, a right arm, a left side, and a right side. In an example, the positional values include a distance between a pair of the plurality of ultrasonic positioning sensors. In an example, the positional values include a ratio of a first distance between a first pair of the plurality of ultrasonic positioning sensors and a second distance between a second pair of the plurality of ultrasonic positioning sensors.

At 1110, at least some of a plurality of feedback devices secured with respect to the fabric are caused to output the feedback signal based, at least in part, on a difference between the positional values as determined and a parameter set of the activity program. In an example, each one of the plurality of feedback devices comprises at least one haptic motor. In an example, the second set of locations comprise a left shoulder, a right shoulder, a left ribcage, a right ribcage, a left hip, a right hip, a midriff, a tailbone, a left knee, and a right knee. In an example, causing the at least some of the plurality of feedback devices comprises causing individual ones of the plurality of feedback devices to output the feedback signal to induce the wearer of the article of apparel to change posture. In an example, the parameter set comprises at least one target value indicative of a desired distance between two or more of the plurality of positioning sensors, and wherein causing the individual ones of the plurality of feedback devices to output the feedback signal is based on a variation between an associated positional value and the target value. In an example, the target value is associated with a tolerance value and wherein causing the individual ones of the plurality of feedback devices to output the feedback signal is based on the variation exceeding the tolerance value. In an example, causing at least some of a plurality of feedback devices to output the feedback signal includes outputting the feedback signal based, at least in part, on a signal from the respiration sensor secured with respect to the fabric.

EXAMPLES

In Example 1, an article of apparel includes a fabric configured to conform to a body of a wearer, a plurality of ultrasonic positioning sensors secured with respect to the fabric at a first set of predetermined locations, each of the ultrasonic positioning sensors configured to emit a sound wave configured to be detected by other ones of the plurality of ultrasonic positioning sensors and output an electronic signal indicative of having emitted or detected a sound wave, and a plurality of feedback devices secured with respect to the fabric at a second set of predetermined locations, each of the feedback devices configured to output a feedback signal configured to be detectable by the wearer of the article of apparel. A processor is configured to determine positional values of the plurality of ultrasonic positioning sensors based, at least in part, on electronic signals output by the plurality of ultrasonic positioning sensors and cause at least some of the plurality of feedback devices to output the feedback signal based, at least in part, on a difference between the positional values as determined and a parameter set of an activity program.

In Example 2, the article of apparel of Example 1 optionally further includes that the first set of locations comprise a left shoulder, a right shoulder, a left arm, a right arm, a left side, and a right side.

In Example 3, the article of apparel of any one or more of Examples 1 and 2 optionally further includes that the positional values include a distance between a pair of the plurality of ultrasonic positioning sensors.

In Example 4, the article of apparel of any one or more of Examples 1-3 optionally further includes that the positional values include a ratio of a first distance between a first pair of the plurality of ultrasonic positioning sensors and a second distance between a second pair of the plurality of ultrasonic positioning sensors.

In Example 5, the article of apparel of any one or more of Examples 1-4 optionally further includes that each one of the plurality of feedback devices comprises at least one haptic motor.

In Example 6, the article of apparel of any one or more of Examples 1-5 optionally further includes that the second set of locations comprise a left shoulder, a right shoulder, a left ribcage, a right ribcage, a left hip, a right hip, a midriff, a tailbone, a left knee, and a right knee.

In Example 7, the article of apparel of any one or more of Examples 1-6 optionally further includes that the processor is configured to cause individual ones of the plurality of feedback devices to output the feedback signal to induce the wearer of the article of apparel to change posture.

In Example 8, the article of apparel of any one or more of Examples 1-7 optionally further includes that the parameter set comprises at least one target value indicative of a desired distance between two or more of the plurality of positioning sensors, and wherein the processor is configured to cause the individual ones of the plurality of feedback devices to output the feedback signal based on a variation between an associated positional value and the target value.

In Example 9, the article of apparel of any one or more of Examples 1-8 optionally further includes that the target value is associated with a tolerance value and wherein the processor is configured to cause the individual ones of the plurality of feedback devices to output the feedback signal based on the variation exceeding the tolerance value.

In Example 10, the article of apparel of any one or more of Examples 1-9 optionally further includes a respiration sensor secured with respect to the fabric and configured to output a signal based, at least in part, on physiologic factors indicative of respiration of the wearer of the article of apparel, wherein the processor is further configured to cause at least some of the plurality of feedback devices to output the feedback signal based, at least in part, on the signal from the respiration sensor.

In Example 11, the article of apparel of any one or more of Examples 1-10 optionally further includes the processor, secured with respect to the fabric and coupled to the plurality of ultrasonic positioning sensors and the plurality of feedback devices.

In Example 12, the article of apparel of any one or more of Examples 1-11 optionally further includes a wireless receiver, secured with respect to the fabric and coupled to the processor, configured to receive the activity program from a wireless transmitter and an electronic data storage, secured with respect to the fabric and coupled to the processor, configured to store the activity program as received by the wireless receiver, wherein the processor is configured to access the activity program from the electronic data storage.

In Example 13, the article of apparel of any one or more of Examples 1-12 optionally further includes a first wireless antenna, secured with respect to the fabric and coupled to the plurality of ultrasonic positioning sensors and the plurality of feedback devices, configured to establish a wireless connection with a second wireless antenna coupled to the processor, wherein the plurality of ultrasonic positioning sensors and the plurality of feedback devices are communicatively coupleable to the processor via the wireless connection and a holder, secured with respect to the fabric, configured to secure, at least in part, a mobile device, the mobile device comprising the processor and the second wireless antenna.

In Example 14, the article of apparel of any one or more of Examples 1-13 optionally further includes that the first and second wireless antenna are configured to communicate via a near field communication (NFC) wireless modality.

In Example 15, the article of apparel of any one or more of Examples 1-14 optionally further includes that the activity program comprises a plurality of parameter sets, including the parameter set, sequentially organized over time, each discrete period of time corresponding to not more than one of the plurality of parameter sets.

In Example 16, the article of apparel of any one or more of Examples 1-15 optionally further includes that the parameter set comprises at least one target value indicative of a desired distance between two or more of the plurality of positioning sensors, and wherein the processor is configured to cause the individual ones of the plurality of feedback devices to output the feedback signal based on a variation between an associated positional value and the target value.

In Example 17, the article of apparel of any one or more of Examples 1-16 optionally further includes that the activity program is synchronized with an instructional video and wherein individual parameter sets individually correspond to predetermined times in the instructional video.

In Example 18, the article of apparel of any one or more of Examples 1-17 optionally further includes that each individual parameter set is configured to reflect a corresponding instruction at an associated predetermined time in the instructional video.

In Example 19, a method includes forming a fabric to conform to a body of a wearer, securing a plurality of ultrasonic positioning sensors with respect to the fabric at a first set of predetermined locations, each of the ultrasonic positioning sensors configured to emit a sound wave configured to be detected by other ones of the plurality of ultrasonic positioning sensors and output an electronic signal indicative of having emitted or detected a sound wave, the electronic signal configured to be utilized by a processor to determine positional values, and securing a plurality of feedback devices with respect to the fabric at a second set of predetermined locations, each of the feedback devices configured to output a feedback signal configured to be detectable by the wearer of the article of apparel based on a difference between the positional values as determined and a parameter set of an activity program.

In Example 20, the method of Example 19 optionally further includes that the first set of locations comprise a left shoulder, a right shoulder, a left arm, a right arm, a left side, and a right side.

In Example 21, the method of any one or more of Examples 19 and 20 optionally further includes that the positional values include a distance between a pair of the plurality of ultrasonic positioning sensors.

In Example 22, the method of any one or more of Examples 19-21 optionally further includes that the positional values include a ratio of a first distance between a first pair of the plurality of ultrasonic positioning sensors and a second distance between a second pair of the plurality of ultrasonic positioning sensors.

In Example 23, the method of any one or more of Examples 19-22 optionally further includes that each one of the plurality of feedback devices comprises at least one haptic motor.

In Example 24, the method of any one or more of Examples 19-23 optionally further includes that the second set of locations comprise a left shoulder, a right shoulder, a left ribcage, a right ribcage, a left hip, a right hip, a midriff, a tailbone, a left knee, and a right knee.

In Example 25, the method of any one or more of Examples 19-24 optionally further includes that individual ones of the plurality of feedback devices are configured to output the feedback signal to induce the wearer of the article of apparel to change posture.

In Example 26, the method of any one or more of Examples 19-25 optionally further includes that the parameter set comprises at least one target value indicative of a desired distance between two or more of the plurality of positioning sensors, and wherein the individual ones of the plurality of feedback devices are configured to output the feedback signal based on a variation between an associated positional value and the target value.

In Example 27, the method of any one or more of Examples 19-26 optionally further includes that the target value is associated with a tolerance value and wherein the processor is configured to cause the individual ones of the plurality of feedback devices to output the feedback signal based on the variation exceeding the tolerance value.

In Example 28, the method of any one or more of Examples 19-27 optionally further includes securing a respiration sensor with respect to the fabric and configured to output a signal based, at least in part, on physiologic factors indicative of respiration of the wearer of the article of apparel, wherein at least some of the plurality of feedback devices are configured to output the feedback signal based, at least in part, on the signal from the respiration sensor.

In Example 29, the method of any one or more of Examples 19-28 optionally further includes securing the processor with respect to the fabric and coupled to the plurality of ultrasonic positioning sensors and the plurality of feedback devices.

In Example 30, the method of any one or more of Examples 19-29 optionally further includes securing a wireless receiver with respect to the fabric and coupled to the processor, configured to receive the activity program from a wireless transmitter and securing an electronic data storage with respect to the fabric and coupled to the processor, configured to store the activity program as received by the wireless receiver, wherein the processor is configured to access the activity program from the electronic data storage.

In Example 31, the method of any one or more of Examples 19-30 optionally further includes securing a first wireless antenna with respect to the fabric and coupled to the plurality of ultrasonic positioning sensors and the plurality of feedback devices, configured to establish a wireless connection with a second wireless antenna coupled to the processor, wherein the plurality of ultrasonic positioning sensors and the plurality of feedback devices are communicatively coupleable to the processor via the wireless connection and securing a holder with respect to the fabric, configured to secure, at least in part, a mobile device, the mobile device comprising the processor and the second wireless antenna.

In Example 32, the method of any one or more of Examples 19-31 optionally further includes that the first and second wireless antenna are configured to communicate via a near field communication (NFC) wireless modality.

In Example 33, the method of any one or more of Examples 19-32 optionally further includes that the activity program comprises a plurality of parameter sets, including the parameter set, sequentially organized over time, each discrete period of time corresponding to not more than one of the plurality of parameter sets.

In Example 34, the method of any one or more of Examples 19-33 optionally further includes that the parameter set comprises at least one target value indicative of a desired distance between two or more of the plurality of positioning sensors, and wherein the processor is configured to cause the individual ones of the plurality of feedback devices to output the feedback signal based on a variation between an associated positional value and the target value.

In Example 35, the method of any one or more of Examples 19-34 optionally further includes that the activity program is synchronized with an instructional video and wherein individual parameter sets individually correspond to predetermined times in the instructional video.

In Example 36, the method of any one or more of Examples 19-35 optionally further includes that each individual parameter set is configured to reflect a corresponding instruction at an associated predetermined time in the instructional video.

In Example 37, a method includes determining, with a processor, positional values of a plurality of ultrasonic positioning sensors secured with respect to a fabric at a first set of predetermined locations based, at least in part, on electronic signals output by the plurality of ultrasonic positioning sensors, wherein the fabric is configured to conform to a body of a wearer and causing at least some of a plurality of feedback devices secured with respect to the fabric to output the feedback signal based, at least in part, on a difference between the positional values as determined and a parameter set of an activity program.

In Example 38, the method of Example 37 optionally further includes that the first set of locations comprise a left shoulder, a right shoulder, a left arm, a right arm, a left side, and a right side.

In Example 39, the method of any one or more of Examples 37 and 38 optionally further includes that the positional values include a distance between a pair of the plurality of ultrasonic positioning sensors.

In Example 40, the method of any one or more of Examples 37-39 optionally further includes that the positional values include a ratio of a first distance between a first pair of the plurality of ultrasonic positioning sensors and a second distance between a second pair of the plurality of ultrasonic positioning sensors.

In Example 41, the method of any one or more of Examples 37-40 optionally further includes that each one of the plurality of feedback devices comprises at least one haptic motor.

In Example 42, the method of any one or more of Examples 37-41 optionally further includes that the second set of locations comprise a left shoulder, a right shoulder, a left ribcage, a right ribcage, a left hip, a right hip, a midriff, a tailbone, a left knee, and a right knee.

In Example 43, the method of any one or more of Examples 37-42 optionally further includes that causing the at least some of the plurality of feedback devices comprises causing individual ones of the plurality of feedback devices to output the feedback signal to induce the wearer of the article of apparel to change posture.

In Example 44, the method of any one or more of Examples 37-43 optionally further includes that the parameter set comprises at least one target value indicative of a desired distance between two or more of the plurality of positioning sensors, and wherein causing the individual ones of the plurality of feedback devices to output the feedback signal is based on a variation between an associated positional value and the target value.

In Example 45, the method of any one or more of Examples 37-44 optionally further includes that the target value is associated with a tolerance value and wherein causing the individual ones of the plurality of feedback devices to output the feedback signal is based on the variation exceeding the tolerance value.

In Example 46, the method of any one or more of Examples 37-45 optionally further includes that causing at least some of a plurality of feedback devices to output the feedback signal includes outputting the feedback signal based, at least in part, on a signal from the respiration sensor secured with respect to the fabric.

In Example 47, the method of any one or more of Examples 37-46 optionally further includes receiving, via a wireless receiver, the activity program from a wireless transmitter and storing the activity program in an electronic data storage the activity program as received by the wireless receiver, wherein the processor is configured to access the activity program from the electronic data storage.

In Example 48, the method of any one or more of Examples 37-47 optionally further includes establishing a wireless connection between a first wireless antenna secured to the fabric and a second wireless antenna coupled to the processor, wherein the plurality of ultrasonic positioning sensors and the plurality of feedback devices are communicatively coupleable to the processor via the wireless connection and securing a mobile device, at least in part, with respect to the fabric, the mobile device comprising the processor and the second wireless antenna.

In Example 49, the method of any one or more of Examples 37-48 optionally further includes establishing the wireless connection is via a near field communication (NFC) wireless modality.

In Example 50, the method of any one or more of Examples 37-49 optionally further includes that the activity program comprises a plurality of parameter sets, including the parameter set, sequentially organized over time, each discrete period of time corresponding to not more than one of the plurality of parameter sets.

In Example 51, the method of any one or more of Examples 37-50 optionally further includes that the parameter set comprises at least one target value indicative of a desired distance between two or more of the plurality of positioning sensors, and wherein causing the individual ones of the plurality of feedback devices to output the feedback signal is based on a variation between an associated positional value and the target value.

In Example 52, the method of any one or more of Examples 37-51 optionally further includes that the activity program is synchronized with an instructional video and wherein individual parameter sets individually correspond to predetermined times in the instructional video.

In Example 53, the method of any one or more of Examples 37-52 optionally further includes that each individual parameter set is configured to reflect a corresponding instruction at an associated predetermined time in the instructional video.

In Example 54, a system includes a fabric configured to conform to a body of a wearer, a plurality of ultrasonic positioning sensors secured with respect to the fabric at a first set of predetermined locations, each of the ultrasonic positioning sensors configured to emit a sound wave configured to be detected by other ones of the plurality of ultrasonic positioning sensors and output an electronic signal indicative of having emitted or detected a sound wave, and a plurality of feedback devices secured with respect to the fabric at a second set of predetermined locations, each of the feedback devices configured to output a feedback signal configured to be detectable by the wearer of the article of apparel. A processor is configured to determine positional values of the plurality of ultrasonic positioning sensors based, at least in part, on electronic signals output by the plurality of ultrasonic positioning sensors and cause at least some of the plurality of feedback devices to output the feedback signal based, at least in part, on a difference between the positional values as determined and a parameter set of an activity program.

In Example 55, the system of Example 54 optionally further includes that the first set of locations comprise a left shoulder, a right shoulder, a left arm, a right arm, a left side, and a right side.

In Example 56, the system of any one or more of Examples 54 and 55 optionally further includes that the positional values include a distance between a pair of the plurality of ultrasonic positioning sensors.

In Example 57, the system of any one or more of Examples 54-56 optionally further includes that the positional values include a ratio of a first distance between a first pair of the plurality of ultrasonic positioning sensors and a second distance between a second pair of the plurality of ultrasonic positioning sensors.

In Example 58, the system of any one or more of Examples 54-57 optionally further includes that each one of the plurality of feedback devices comprises at least one haptic motor.

In Example 59, the system of any one or more of Examples 54-58 optionally further includes that the second set of locations comprise a left shoulder, a right shoulder, a left ribcage, a right ribcage, a left hip, a right hip, a midriff, a tailbone, a left knee, and a right knee.

In Example 60, the system of any one or more of Examples 54-59 optionally further includes that the processor is configured to cause individual ones of the plurality of feedback devices to output the feedback signal to induce the wearer of the article of apparel to change posture.

In Example 61, the system of any one or more of Examples 54-60 optionally further includes that the parameter set comprises at least one target value indicative of a desired distance between two or more of the plurality of positioning sensors, and wherein the processor is configured to cause the individual ones of the plurality of feedback devices to output the feedback signal based on a variation between an associated positional value and the target value.

In Example 62, the system of any one or more of Examples 54-61 optionally further includes that the target value is associated with a tolerance value and wherein the processor is configured to cause the individual ones of the plurality of feedback devices to output the feedback signal based on the variation exceeding the tolerance value.

In Example 63, the system of any one or more of Examples 54-62 optionally further includes a respiration sensor secured with respect to the fabric and configured to output a signal based, at least in part, on physiologic factors indicative of respiration of the wearer of the article of apparel, wherein the processor is further configured to cause at least some of the plurality of feedback devices to output the feedback signal based, at least in part, on the signal from the respiration sensor.

In Example 64, the system of any one or more of Examples 54-63 optionally further includes that the processor is secured with respect to the fabric and coupled to the plurality of ultrasonic positioning sensors and the plurality of feedback devices.

In Example 65, the system of any one or more of Examples 54-64 optionally further includes a wireless receiver, secured with respect to the fabric and coupled to the processor, configured to receive the activity program from a wireless transmitter and an electronic data storage, secured with respect to the fabric and coupled to the processor, configured to store the activity program as received by the wireless receiver, wherein the processor is configured to access the activity program from the electronic data storage.

In Example 66, the system of any one or more of Examples 54-65 optionally further includes a first wireless antenna, secured with respect to the fabric and coupled to the plurality of ultrasonic positioning sensors and the plurality of feedback devices, configured to establish a wireless connection with a second wireless antenna coupled to the processor, wherein the plurality of ultrasonic positioning sensors and the plurality of feedback devices are communicatively coupleable to the processor via the wireless connection and a holder, secured with respect to the fabric, configured to secure, at least in part, a mobile device, the mobile device comprising the processor and the second wireless antenna.

In Example 67, the system of any one or more of Examples 54-66 optionally further includes that the first and second wireless antennas are configured to communicate via a near field communication (NFC) wireless modality.

In Example 68, the system of any one or more of Examples 54-67 optionally further includes that the activity program comprises a plurality of parameter sets, including the parameter set, sequentially organized over time, each discrete period of time corresponding to not more than one of the plurality of parameter sets.

In Example 69, the system of any one or more of Examples 54-68 optionally further includes that the parameter set comprises at least one target value indicative of a desired distance between two or more of the plurality of positioning sensors, and wherein the processor is configured to cause the individual ones of the plurality of feedback devices to output the feedback signal based on a variation between an associated positional value and the target value.

In Example 70, the system of any one or more of Examples 54-69 optionally further includes that the activity program is synchronized with an instructional video and wherein individual parameter sets individually correspond to predetermined times in the instructional video and further comprising a display configured to display the instructional video.

In Example 71, the system of any one or more of Examples 54-70 optionally further includes that each individual parameter set is configured to reflect a corresponding instruction at an associated predetermined time in the instructional video.

As used herein, the term "memory" refers to a machine-readable medium able to store data temporarily or permanently and may be taken to include, but not be limited to, random-access memory (RAM), read-only memory (ROM), buffer memory, flash memory, ferroelectric RAM (FRAM), and cache memory. The term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of storing instructions (e.g., software) for execution by a machine, such that the instructions, when executed by one or more processors of the machine, cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" shall accordingly be taken to include, but not be limited to, one or more data repositories in the form of a solid-state memory, an optical medium, a magnetic medium, or any suitable combination thereof.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, or mechanisms. Modules may constitute either software modules (e.g., code embodied on a machine-readable medium or in a transmission signal) or hardware modules. A "hardware module" is a tangible unit capable of performing certain operations and may be configured or arranged in a certain physical manner. In various example embodiments, one or more computer systems (e.g., a standalone computer system, a client computer system, or a server computer system) or one or more hardware modules of a computer system (e.g., a processor or a group of processors) may be configured by software (e.g., an application or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a field programmable gate array (FPGA) or an ASIC. A hardware module may also include programmable logic or circuitry that is temporarily configured by software to perform certain operations. For example, a hardware module may include software encompassed within a general-purpose processor or other programmable processor. It will be appreciated that the decision to implement a hardware module mechanically, in dedicated and permanently configured circuitry, or in temporarily configured circuitry (e.g., configured by software) may be driven by cost and time considerations.

Accordingly, the phrase "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where a hardware module comprises a general-purpose processor configured by software to become a special-purpose processor, the general-purpose processor may be configured as respectively different special-purpose processors (e.g., comprising different hardware modules) at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple hardware modules exist contemporaneously, communications may be achieved through signal transmission (e.g., over appropriate circuits and buses) between or among two or more of the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module implemented using one or more processors.

Similarly, the methods described herein may be at least partially processor-implemented, a processor being an example of hardware. For example, at least some of the operations of a method may be performed by one or more processors or processor-implemented modules. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an application program interface (API)).

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or any suitable combination thereof), registers, or other machine components that receive, store, transmit, or display information. Furthermore, unless specifically stated otherwise, the terms "a" or "an" are herein used, as is common in patent documents, to include one or more than one instance. Finally, as used herein, the conjunction "or" refers to a non-exclusive "or," unless specifically stated otherwise.

What is claimed is:

1. An article of apparel, comprising:
   a fabric configured to conform to a body of a wearer;
   a plurality of ultrasonic positioning sensors secured with respect to the fabric at a first set of predetermined locations, each of the ultrasonic positioning sensors configured to emit a sound wave configured to be detected by other ones of the plurality of ultrasonic positioning sensors and output an electronic signal indicative of having emitted or detected a sound wave; and a plurality of feedback devices secured with respect to the fabric at a second set of predetermined locations, wherein each of the feedback devices configured to output a feedback signal that is detectable by the wearer of the article of apparel, wherein individual feedback devices of the plurality of feedback devices are configured to provide feedback signals at respective different times according to a predetermined feedback signal sequence;

a processor, configured to:

at a plurality of discrete sequential times, determine positional values of the plurality of ultrasonic positioning sensors based, at least in part, on electronic signals output by the plurality of ultrasonic positioning sensors; and cause at least some of the plurality of feedback devices to output the feedback signal corresponding to one of the plurality of predetermined sequences based, at least in part, on a difference between the positional values as determined at the plurality of discrete sequential times and a parameter set of an activity program.

2. The article of apparel of claim 1, wherein the parameter set comprises at least one target value indicative of a desired distance between two or more of the plurality of positioning sensors, and wherein the processor is configured to cause the individual ones of the plurality of feedback devices to output the feedback signal based on a variation between an associated positional value and the target value.

3. The article of apparel of claim 2, wherein the processor is configured to cause the individual ones of the plurality of feedback devices to output the feedback signal when the variation exceeds a tolerance margin of the target value.

4. The article of apparel of claim 1, wherein at least one of the predetermined sequences incudes a variable intensity of the feedback signal provided by at least one of the plurality of feedback devices.

5. The article of apparel of claim 4, wherein the variable intensity is based, at least in part, on a degree of deviation from the activity program.

6. The article of apparel of claim 1, wherein at least one of the predetermined sequences includes providing the feedback signal from only one of the plurality of feedback devices at a time.

7. The article of apparel of claim 1, wherein at least one of the predetermined sequences includes providing the feedback signal from more than one of the plurality of feedback devices at a time.

8. A method, comprising:

determining, with a processor, at a plurality of discrete sequential times, positional values of a plurality of ultrasonic positioning sensors secured with respect to a fabric at a first set of predetermined locations, the positional values based, at least in part, on electronic signals output by the plurality of ultrasonic positioning sensors, wherein the fabric is configured to conform to a body of a wearer; and causing, with the processor, at least some of a plurality of feedback devices to output a feedback signal corresponding to one of a plurality of predetermined sequences based, at least in part, on a difference between the positional values as determined at the plurality of discrete sequential times and a parameter set of an activity program, wherein individual feedback devices of the plurality of feedback devices are configured to provide feedback signals at respective different times according to a predetermined feedback signal sequence.

9. The method of claim 8, wherein the parameter set comprises at least one target value indicative of a desired distance between two or more of the plurality of positioning sensors, and wherein the processor is configured to cause the individual ones of the plurality of feedback devices to output the feedback signal based on a variation between an associated positional value and the target value.

10. The method of claim 9, wherein the processor is configured to cause the individual ones of the plurality of feedback devices to output the feedback signal when the variation exceeds a tolerance margin of the target value.

11. The method of claim 8, wherein at least one of the predetermined sequences incudes a variable intensity of the feedback signal provided by at least one of the plurality of feedback devices.

12. The method of claim 11, wherein the variable intensity is based, at least in part, on a degree of deviation from the activity program.

13. The method of claim 8, wherein at least one of the predetermined sequences includes providing the feedback signal from only one of the plurality of feedback devices at a time.

14. The method of claim 8, wherein at least one of the predetermined sequences includes providing the feedback signal from more than one of the plurality of feedback devices at a time.

15. A system, comprising:

a fabric configured to conform to a body of a wearer;

a plurality of ultrasonic positioning sensors secured with respect to the fabric at a first set of predetermined locations, each of the ultrasonic positioning sensors configured to emit a sound wave configured to be detected by other ones of the plurality of ultrasonic positioning sensors and output an electronic signal indicative of having emitted or detected a sound wave; and a plurality of feedback devices secured with respect to the fabric at a second set of predetermined locations, wherein individual feedback devices of the plurality of feedback devices are configured to provide feedback signals at respective different times according to a predetermined feedback signal sequence; and a processor, configured to:

at a plurality of discrete sequential times, determine positional values of the plurality of ultrasonic positioning sensors based, at least in part, on electronic signals output by the plurality of ultrasonic positioning sensors; and cause at least some of the plurality of feedback devices to output the feedback signal corresponding to one of the plurality of predetermined sequences based, at least in part, on a difference between the positional values as determined at the plurality of discrete sequential times and a parameter set of an activity program.

16. The system of claim 15, wherein the parameter set comprises at least one target value indicative of a desired distance between two or more of the plurality of positioning sensors, and wherein the processor is configured to cause the individual ones of the plurality of feedback devices to output the feedback signal based on a variation between an associated positional value and the target value.

17. The system of claim 16, wherein the processor is configured to cause the individual ones of the plurality of feedback devices to output the feedback signal when the variation exceeds a tolerance margin of the target value.

18. The system of claim 15, wherein at least one of the predetermined sequences incudes a variable intensity of the feedback signal provided by at least one of the plurality of feedback devices.

19. The system of claim 18, wherein the variable intensity is based, at least in part, on a degree of deviation from the activity program.

20. The system of claim 15, wherein at least one of the predetermined sequences includes providing the feedback signal from only one of the plurality of feedback devices at a time.

21. The system of claim 15, wherein at least one of the predetermined sequences includes providing the feedback signal from more than one of the plurality of feedback devices at a time.

* * * * *